(12) United States Patent
Perkins et al.

(10) Patent No.: US 9,408,724 B2
(45) Date of Patent: Aug. 9, 2016

(54) AIR VALVE FOR EXTERNAL PROSTHESIS

(71) Applicants: Matt Perkins, Boise, ID (US); Travis Dean, Boise, ID (US)

(72) Inventors: Matt Perkins, Boise, ID (US); Travis Dean, Boise, ID (US)

(73) Assignee: Coyote Design and Manufacturing, Inc., Boise, ID (US)

( * ) Notice: Subject to any disclaimer, the term of this patent is extended or adjusted under 35 U.S.C. 154(b) by 585 days.

(21) Appl. No.: 13/652,716

(22) Filed: Oct. 16, 2012

(65) Prior Publication Data

US 2013/0282142 A1 Oct. 24, 2013

(51) Int. Cl.
*A61F 2/80* (2006.01)

(52) U.S. Cl.
CPC ............. *A61F 2/80* (2013.01); *A61F 2002/805* (2013.01)

(58) Field of Classification Search
CPC A61F 2/80; A61F 2002/805; A61F 2002/802
See application file for complete search history.

(56) References Cited

U.S. PATENT DOCUMENTS

| | | | |
|---|---|---|---|
| 1,586,015 A | 5/1926 | Underwood | |
| 2,530,285 A | 11/1950 | Catranis | |
| 2,533,404 A | 12/1950 | Sharp et al. | |
| 2,790,180 A | 4/1957 | Hauser | |
| 4,010,052 A | 3/1977 | Edwards | |
| 4,106,745 A | 8/1978 | Carrow | |
| 4,655,779 A | 4/1987 | Janowiak | |
| 5,007,937 A | 4/1991 | Fishman et al. | |
| 5,201,774 A | 4/1993 | Greene | |
| 5,490,537 A | 2/1996 | Hill | |
| 5,658,353 A | 8/1997 | Layton | |
| 5,702,489 A * | 12/1997 | Slemker ..................... | A61F 2/80 623/34 |
| 5,709,017 A | 1/1998 | Hill | |
| 5,807,303 A | 9/1998 | Bays | |
| 6,287,345 B1 | 9/2001 | Slemker et al. | |
| 6,334,876 B1 | 1/2002 | Perkins | |
| 6,361,568 B1 | 3/2002 | Hoerner | |
| 6,436,149 B1 * | 8/2002 | Rincoe ................... | A61F 2/6607 623/47 |
| 6,508,842 B1 | 1/2003 | Caspers | |
| 6,544,292 B1 | 4/2003 | Laghi | |
| 6,613,096 B1 * | 9/2003 | Shirvis ...................... | A61F 2/80 137/542 |
| 6,626,952 B2 | 9/2003 | Janusson et al. | |
| 6,706,364 B2 | 3/2004 | Janusson et al. | |
| 6,761,742 B2 | 7/2004 | Caspers | |
| 6,797,008 B1 | 9/2004 | Arbogast et al. | |
| 6,979,355 B1 * | 12/2005 | Slemker .................... | A61F 2/80 623/34 |
| 7,448,407 B2 | 11/2008 | Alley et al. | |
| 7,993,413 B2 | 8/2011 | Perkins et al. | |
| 8,206,459 B1 * | 6/2012 | Lock ......................... | A61F 2/48 24/303 |
| 8,343,233 B2 | 1/2013 | Perkins et al. | |
| 2003/0078674 A1 * | 4/2003 | Phillips ................. | A61F 2/7843 623/37 |
| 2004/0083008 A1 * | 4/2004 | Molino ..................... | A61F 2/64 623/44 |

(Continued)

*Primary Examiner* — Bruce E Snow
*Assistant Examiner* — Melissa Hoban
(74) *Attorney, Agent, or Firm* — Pedersen & Company, PLLC; Ken J. Pedersen; Barbara S. Pedersen

(57) ABSTRACT

A valve device regulates the air pressure in the space between a residual limb, or liner-covered limb, and a hard socket of an external prosthesis. A manually-controlled air-outlet and -inlet valve may optionally include an automatic one-way valve (or "expulsion" valve). The manually-controlled valve is opened and closed by twisting a handle, to open a two-way air passageway by slightly separating the handle and base portions, or by aligning bores in the handle and base portions. At least one stop surface limits the amount of relative rotation of the handle and base portions of the valve, so that the user need only rotate the handle a small amount, for example, less than 90 degrees, to affect opening or closing the valve.

23 Claims, 18 Drawing Sheets

(56) References Cited

U.S. PATENT DOCUMENTS

| | | |
|---|---|---|
| 2004/0181290 A1 | 9/2004 | Caspers |
| 2004/0260403 A1 | 12/2004 | Patterson et al. |
| 2005/0240282 A1 | 10/2005 | Rush et al. |
| 2007/0005149 A1 | 1/2007 | Egilsson et al. |
| 2007/0112440 A1 | 5/2007 | Perkins et al. |
| 2010/0087931 A1 | 4/2010 | Bogue |
| 2011/0112657 A1* | 5/2011 | Haun ................... A61F 2/80 623/38 |
| 2013/0150982 A1* | 6/2013 | Mosler ................ A61F 2/80 623/34 |

* cited by examiner

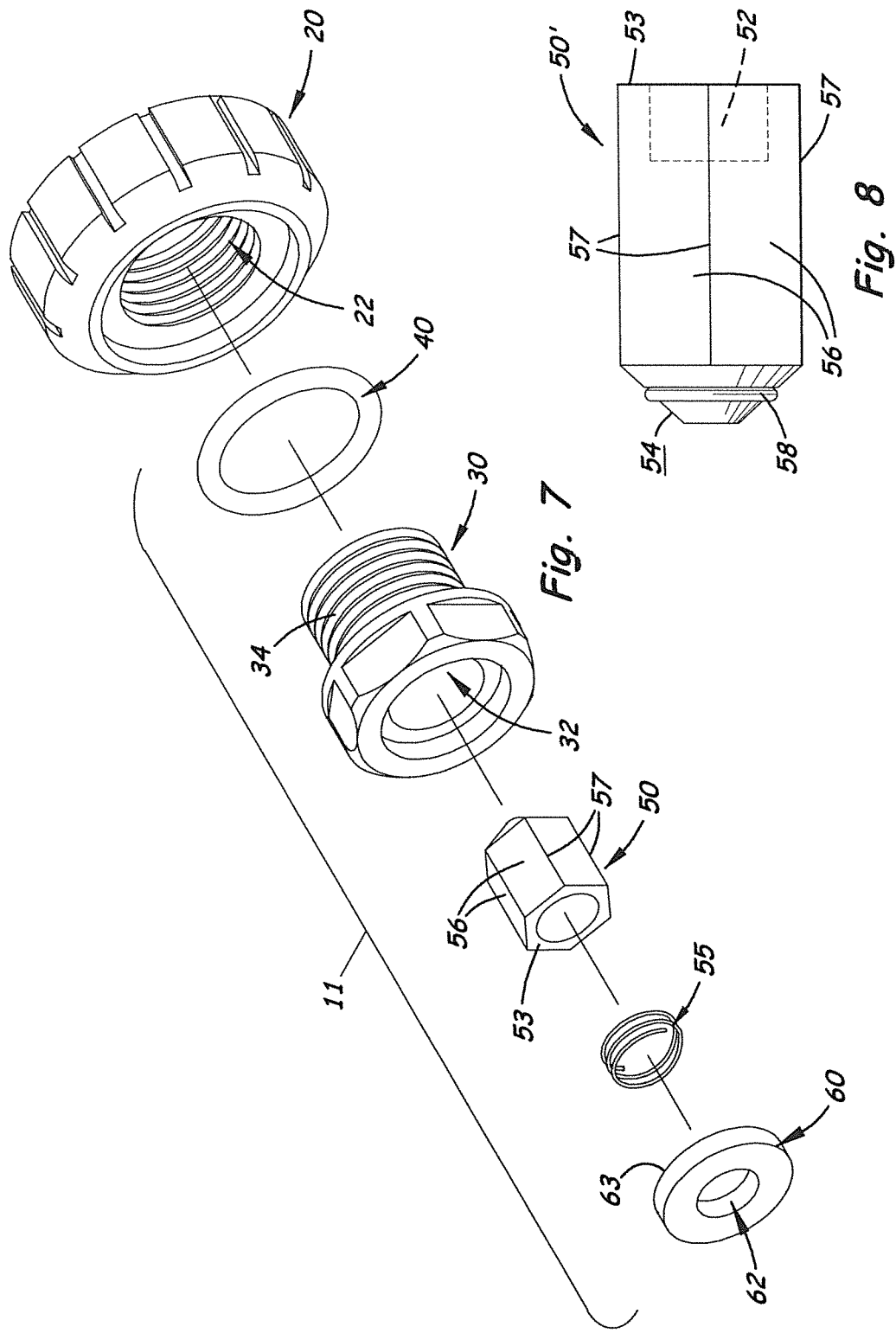

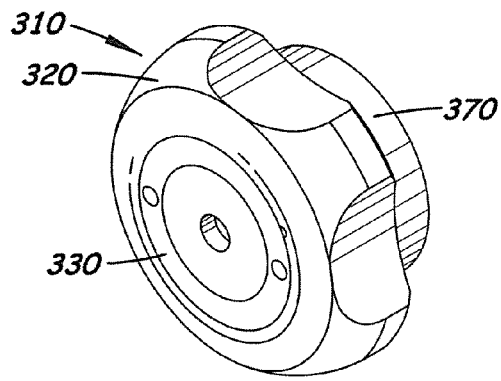
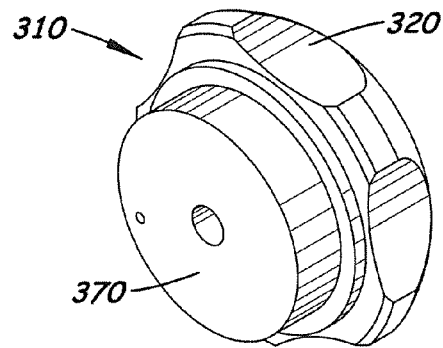
Fig. 20            Fig. 21
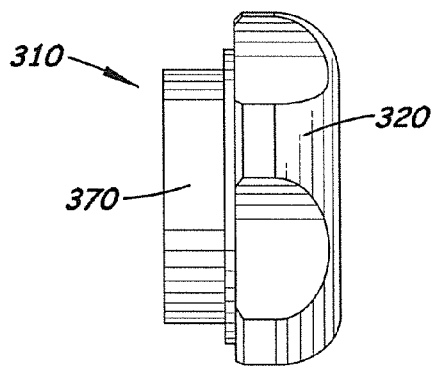
Fig. 22
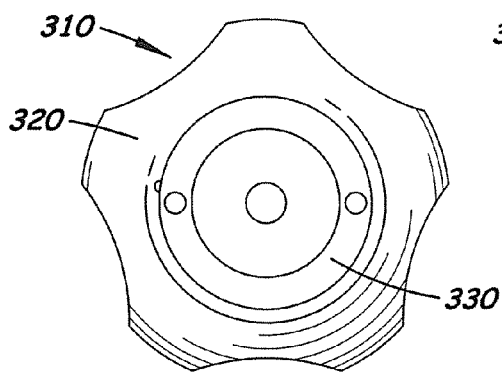
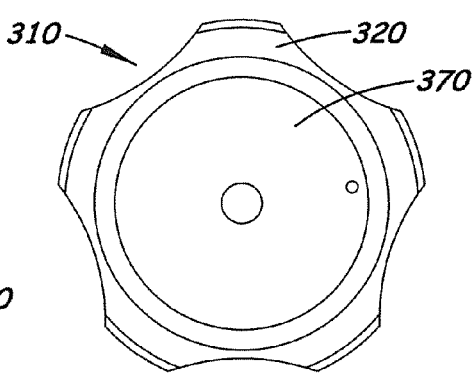
Fig. 23            Fig. 24

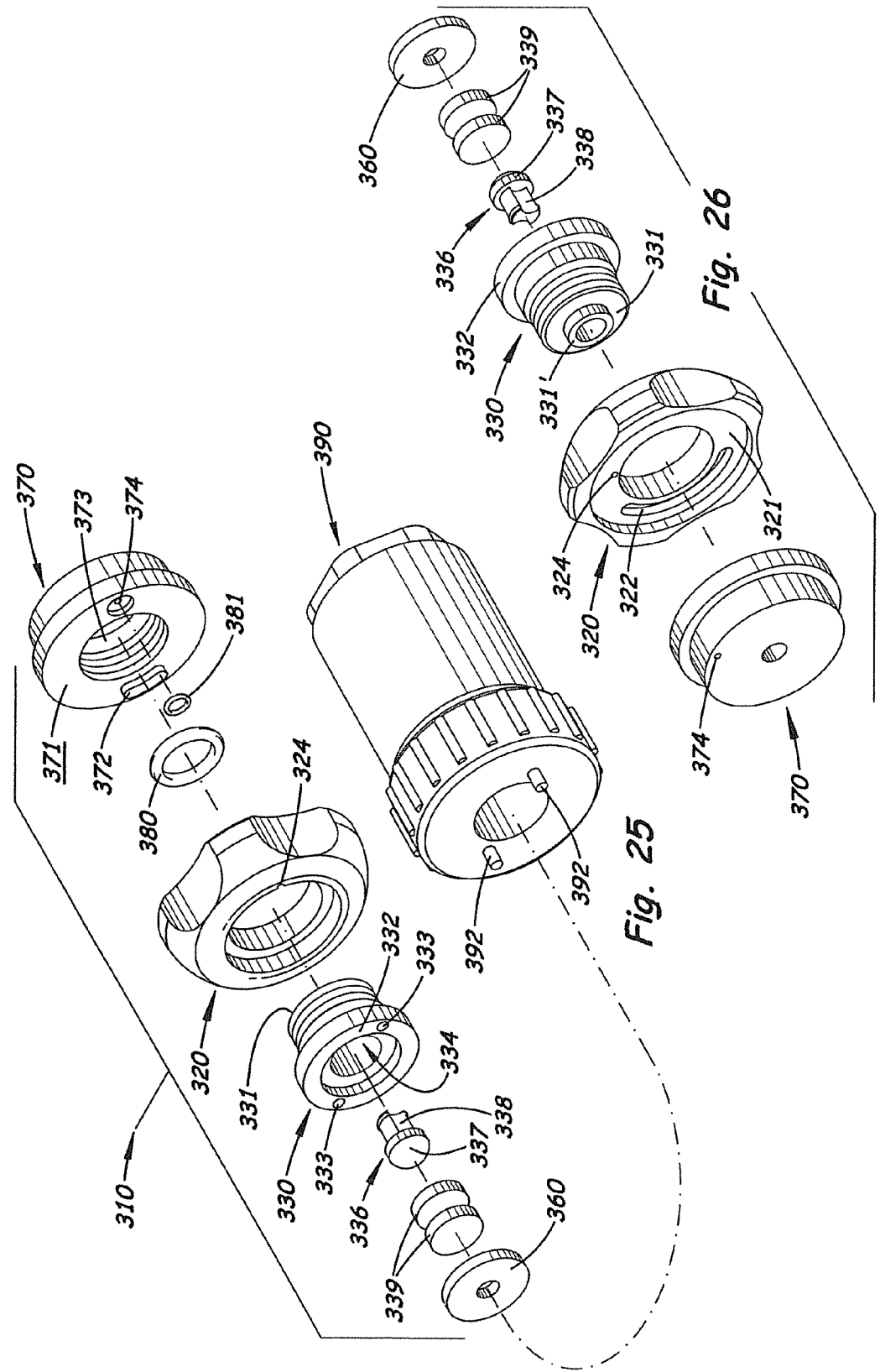

(VALVE CLOSED)

(MANUAL VALVE OPEN)

(VALVE CLOSED)

(CENTER VALVE OPEN)

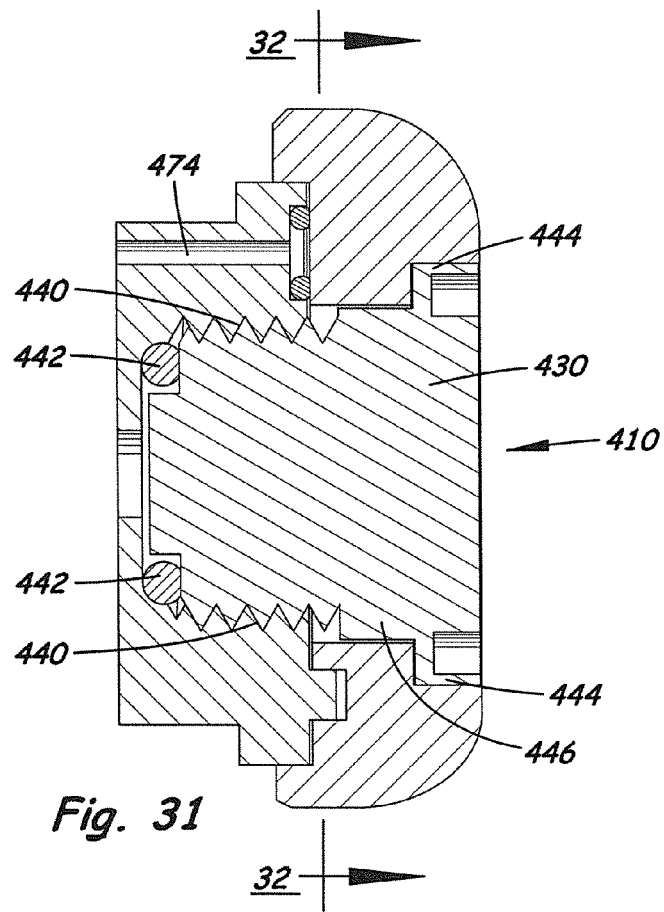
Fig. 31
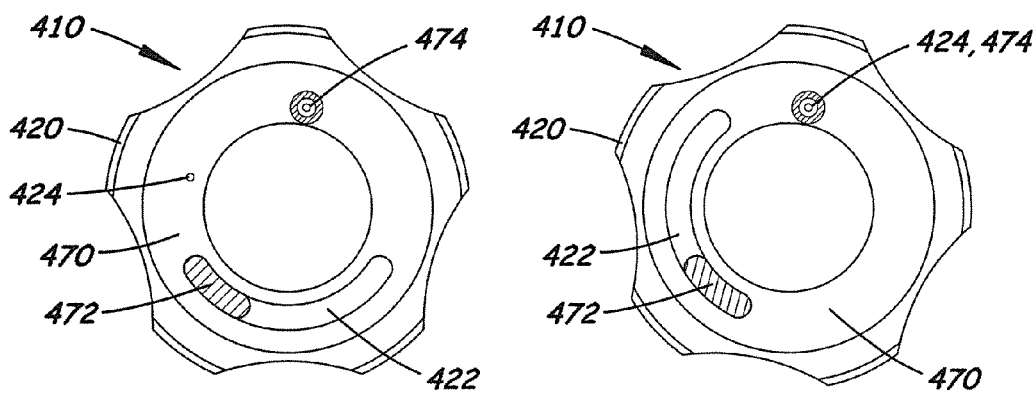
Fig. 32
(VALVE CLOSED)
Fig. 33
(VALVE OPEN)

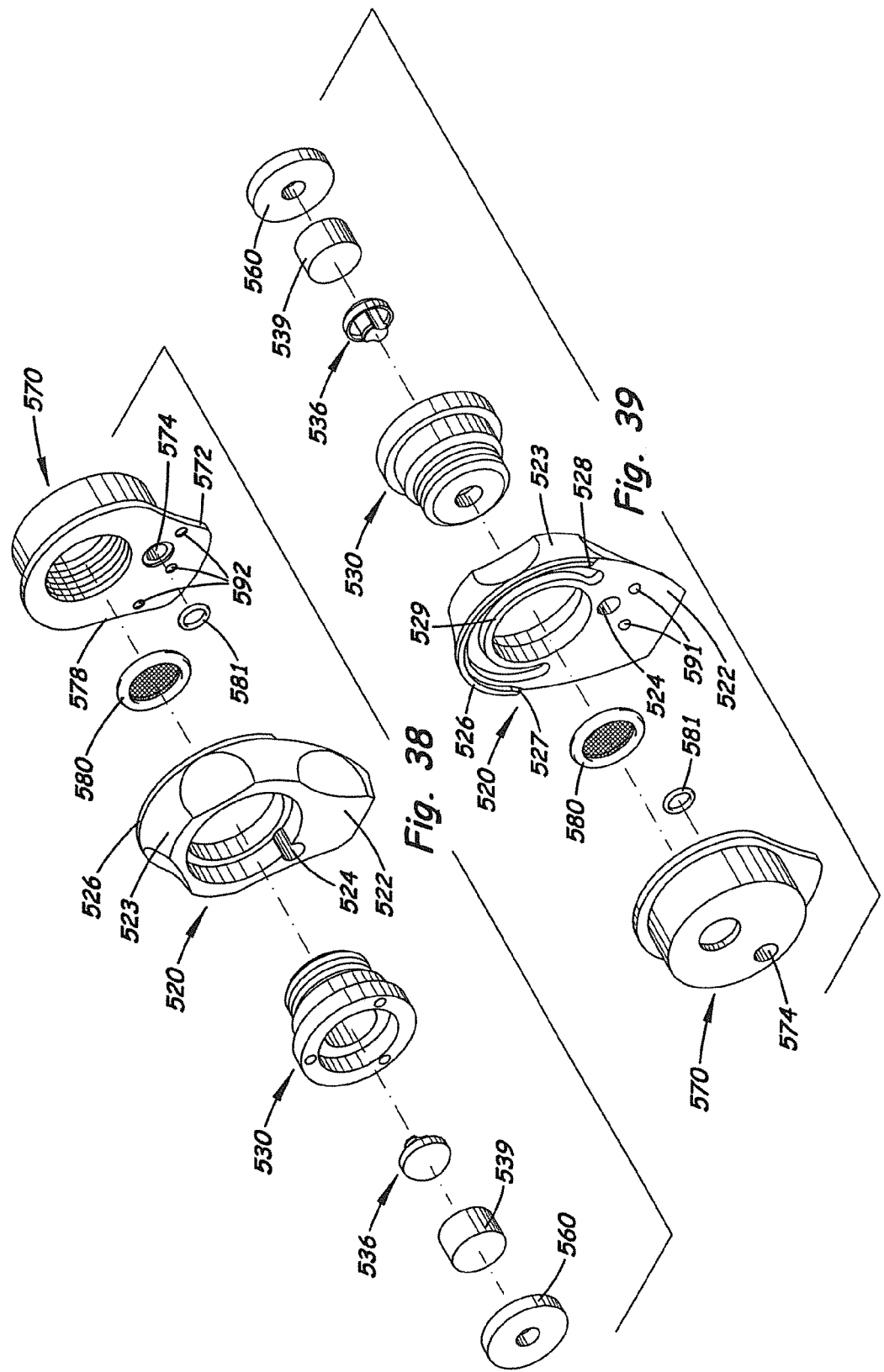

AIR VALVE FOR EXTERNAL PROSTHESIS

The disclosures of the following applications, in their entirety, are incorporated herein by this reference: prior U.S. Non-Provisional application Ser. No. 13/206,489, filed Aug. 9, 2011, U.S. Non-Provisional application Ser. No. 12/364,511, filed Feb. 2, 2009 and issued as U.S. Pat. No. 7,993,413 on Aug. 9, 2011, U.S. Non-provisional application Ser. No. 11/527,752, filed Sep. 25, 2006 and now abandoned, Provisional Application Ser. No. 60/719,785, filed Sep. 24, 2005, and Ser. No. 61/024,913, filed Jan. 31, 2008; and U.S. Non-Provisional application Ser. No. 12/826,633, filed Jun. 29, 2010.

BACKGROUND OF THE INVENTION

1. Field of the Invention

The present invention relates to prosthetics, and more specifically to a valve device for control of pressure in an external prosthetic such as may be used on a residual limb.

2. Related Art

Gravitational and other forces tend to cause separation between a prosthetic limb and a residual limb. This happens, for example, during the swing phase of the gait, when a prosthetic leg is additionally subjected to centrifugal forces. The manner in which an artificial limb is suspended and/or attached to the residual limb determines the amount of control an amputee has over the prosthesis. Patients have routinely worn a variety of belts, straps, cuffs and harnesses to prevent the prosthetic limb from separating from the residual limb, but such devices are inconvenient and tend to cause chafing against the patient's body, giving rise to sores and abrasions.

It has long been appreciated that differential air pressure, often referred by those of skill in the art as "suction," may be utilized to retain or suspend, or assist in retaining or suspending, a prosthetic limb on a patient's residual limb. "Suction suspension" typically involves a hard socket and a cooperating socket liner positioned between the residual limb and the prosthetic socket. The liner is rolled onto the residual limb for a suction, slight compression, and/or gripping connection of the inner gel layer (or otherwise tacky layer) of the liner to the skin of the residual limb. The liner-covered limb is then inserted into the prosthetic socket, and the outer surface/layer of the liner preferably forms a suction, grip, or other interference fit to the socket to interfere with the socket falling off the limb.

Socket liners frequently have been called "suction liners," "gel liners," "roll-on liners" or "suspension liners" and include the "first generation" of gel-layer-only liners, and also the modern "second generation" liners currently preferred by most wearers of prosthetics. These modern liners "second generation" liners typically comprise a thin textile/fabric outer layer that is fixed to the gel-like inner layer (silicone, urethane, or other rubbery/gel-like material). Thus, the second generation of liners is similar to the first generation in its connection to the residual limb, but its connection to, or cooperation with, the socket is modified by the presence of the textile/fabric layer. The term "suction liner" began with the first generation liners, which featured the gel layer contacting both the residual limb (liner's inner surface) and the socket (liner's outer surface), and, therefore, could be used to create a fairly high amount of pressure differential between the inside of the socket (in the "well" of the socket) and the surrounding ambient air. The terms "suction liner" and "suction socket" are still used by many manufacturers, prosthetic technicians, insurance and medicare/medicaid entities, and wearers of prosthetics, even though the modern "second generation" liners, with their textile/fabric outer layers, typically do not form what would be called "true" or "pure" suction with the socket, but rather form what should more accurately be called a "partial suction" with the socket, as further discussed below. See the discussion of suction liners in Janusson, et al. (U.S. Pat. No. 6,706,364) and Janusson, et al. (U.S. Pat. No. 6,626,952).

The preferred gel-like inner layer of a limb liner grips the limb to such an extent that it needs to be rolled-onto the limb from a rolled-up "doughnut" form, rather than pulled on like a sock. When rolled-on, there is little, if any, air remaining between the inner surface of the roll-on liner and the limb, and the roll-on liner is snug against the limb all the way around the circumference of the limb. Also, the inner surface of the roll-on liner is of such material and tacky texture that air will not be able to, or be very unlikely to, enter between the roll-on liner and limb. Thus, the roll-on liner may be said to form a suction fit and/or a slight compression fit with the limb. A distal force on the liner, such as caused by the swing of a gait with a prosthetic leg, may tug on the roll-on liner but typically does not loosen, lower, or remove the liner from the limb.

The hard socket is usually laminated or otherwise fabricated from polyethylene, polypropylene, or other copolymers, for example, and is donned over the liner and the residual limb. A "true" suction fit (allowing high suction, greater amount of vacuum) will be more likely to form, between the liner-sheathed limb and the interior of the socket, if: a) the liner exterior surface is smooth and flexible enough to conform to the contours of the residual limb, for example, non-air-permeable material such as the silicone, urethane, or other rubbery or gel-like material; b) the interior surface of the socket is also smooth and non-air-permeable; and, of course; and c) if the socket has no un-sealed holes or apertures. A "partial" suction fit (allowing lower suction, low amount of vacuum) is more likely to form in the case of modern "second generation" liners, because not all of these conditions are met. For example, although there is preferably a close fit between the contour of the liner-cover limb and the contour of the internal surface of the socket, which provides significant resistance to air entering the socket via the top opening of the socket, still, some air slowly enters the socket through the top of the socket or through a seam, connection, lock or other aperture in the socket, especially during the swing portion of the wearer's gait and during periods of relative inactivity. Air entering the socket through one or more of these locations may then slowly flow through or past the fabric layer of the modern liners, into the distal area of the interior of the socket, that is, the well of the socket.

The "partial" suction fit tends to be more comfortable for many wearers that a "true" or "full" suction fit. In other words, a textile/fabric-covered liner and the resulting "partial" suction tends to be more comfortable than the stronger "tugging" on the residual limb created by the "full" suction of first generation, gel-layer-only liner. A partial suction suspension, however, is difficult to control due to the dynamics of use of the prosthetic. The process of walking and other weight-bearing, therefore, comprises the steps of pushing the limb further into the socket, followed by the swing portion of the gait that tends to pull the socket off the limb. A one-way "check" valve, typically called an "expulsion valve", may be added to the hard socket to allow air expulsion (of the air leaking into the socket) with each weight-bearing step, while preventing air to flow through (in the reverse direction) through the valve into the socket well during the swing portion of the gait. Thus, an object of the expulsion valve is to maintain a slight negative pressure (partial suction) relative to ambient once the socket has been fitted on the residual limb and used. There may be frequent opening and closing of an expulsion valve, perhaps for each, or for many, of the user's steps. The expulsion valve may also expel air from the socket well as a wearer dons the socket. Conventional expulsion valves for these applications are known to not work very well, to plug easily, or to make embarrassing noise with each step as the air is expelled.

Typical expulsion valves comprise an inner base inserted from the inside of the socket and passing from the inside of the socket to the outside of the socket. The outer housing and the valve components are then threaded onto the inner base or threaded to the socket wall in an attempt to create an air-tight seal between the valve and the socket wall. Such expulsion valves require a generally flat and thick socket wall surface for proper installation, otherwise air tends to leak out of the socket around the expulsion valve.

Issued patents and patent publications relating to valves are listed as follows: Underwood (U.S. Pat. No. 1,586,015), Catranis (U.S. Pat. No. 2,530,285), Sharp et al. (U.S. Pat. No. 2,533,404), Hauser (U.S. Pat. No. 2,790,180), Edwards (U.S. Pat. No. 4,010,052), Carrow (U.S. Pat. No. 4,106,745), Greene (U.S. Pat. No. 5,201,774), Hill (U.S. Pat. No. 5,490,537), Hill (U.S. Pat. No. 5,709,017), Slemker et al. (U.S. Pat. No. 6,287,345), Perkins (U.S. Pat. No. 6,334,876), Hoerner (U.S. Pat. No. 6,361,568), Caspers (U.S. Pat. No. 6,508,842), Laghi (U.S. Pat. No. 6,544,292), Caspers (U.S. Pat. No. 6,761,742), Abrogast et al. (U.S. Pat. No. 6,797,008), Caspers (U.S. Publication No. 2004/0181290), and Patterson et al. (U.S. Publication No. 2004/0260403).

SUMMARY OF THE INVENTION

The present invention is a valve device for helping to regulate the air pressure in the space(s) between a residual limb, or liner-covered limb, and a hard socket of an external prosthesis. The valve device may be used to regulate said air pressure for improved donning and doffing the prosthesis, and/or during walking and other normal use of the prosthesis.

Valve devices according to certain embodiments of the invention comprise a manually-controlled air-outlet and -inlet valve that may be installed on a distal region of a hard socket, and also, in certain embodiments, an automatic one-way air-outlet valve (or "expulsion" valve). The manually-controlled valve may be used to open the socket well to the outside air by providing an air passage from a distal region of the socket well, so that, when the wearer inserts his/her residual limb into the socket, air is pushed out through the manual valve rather than building up pressure inside the socket. Also, when a user wishes to doff the prosthetic, he/she may manually open the valve to allow air to flow through the valve device into the socket, equalizing the air pressure inside and outside the socket, for easier removal of the limb.

The manually-controlled air-outlet and -inlet valve is opened and closed in certain embodiments by twisting of a handle portion of the valve device, wherein partial rotation of the handle portion relative to the base portion of the valve device opens a passageway for air to flow out from the well of the socket, by slightly separating the handle and base portions or by aligning bores in the handle and base portions. This simple twisting, or partial rotation, allows sure and repeatable control of the manual valve, which stays in either the open or closed position without the user's hand holding the valve in that position. Thus, after opening the manual valve, the valve stays in hands-free open status, while the wearer may use his/her hands to don or doff the prosthesis. The manual valve may comprise a system for preventing the moveable handle from becoming entirely separated from the base during normal use, so that the handle portion does not fall off of the prosthesis. Also, in certain embodiments, the manual valve comprises a stop (s) that limit(s) the amount of relative rotation of the handle and base portions of the valve, so that the user need only rotate the handle a small amount, for example, less than 90 degrees, to affect opening or closing the valve. The stop(s) may be part of the system for preventing the handle and base from entirely separating, or may be provided in addition to said system for preventing.

In certain embodiments, the valve device comprises only said manual valve, while in other embodiments, the valve device comprises both a manual valve and an automatic one-way air-outlet valve. In yet other, less-preferred embodiments, the valve device may comprise only the automatic one-way air-outlet valve.

In embodiments comprising the automatic air-outlet valve (also, the "one-way" or "check" valve) a rigid stem or elastic valve member opens ("pops") at a small differential pressure, for example, a pressure inside the socket (in the distal space(s) between said socket and the limb or liner-covered limb) that is less than or equal to 3 psi pressure above ambient pressure (outside the socket). Embodiments having a rigid valve stem and embodiments having an elastic member are illustrated herein, with the latter being currently preferred because of their surprising consistency and effectiveness.

Certain embodiments of the valve device may be adhesively mounted on the outside of the socket, or in an aperture in the socket but extending only partially into the socket wall. These embodiments are easier to mount and maintain compared to conventional valves due to adhesive mounting, preferably no part of the valve device being installed from the inside of the socket, and cleaning/replacement of the one-way valve components being possible entirely from the outside of the socket. The inventors envision, however, that certain embodiments of the invented valve device may be attached to a hard socket by other means. For example, conventional mounting systems for air expulsion valves in the industry, as discussed in the Related Art section above, may allow a valve device with some of the invented features to be used in a format wherein the valve device is connected to a base that protrudes or resides inside the hard socket.

In certain embodiments comprising a one-way air outlet valve, the one-way valve member has a polygonal surface or axial grooves or other recesses in its side wall(s) to create axial passages through which air may flow quietly. Alternatively but less preferably, the valve member may be cylindrical and the channel in which the valve stem slides (the valve housing bore) may be polygonal or have recesses/grooves in its wall(s) to create axial passage(s) through which air may flow quietly. Or, both valve member and the housing bore may be non-cylindrical. The preferred low-profile, substantially-external-mounting, and the quiet action and quiet air flow of the one-way valve results in a less intrusive and less noticeable apparatus than is more acceptable and less embarrassing to wearers during walking and other normal use.

BRIEF DESCRIPTION OF THE DRAWINGS

FIG. 7 is an exploded perspective view of the valve embodiment shown in FIGS. 1-6.

FIG. 8 is an alternative embodiment of a valve stem that may be used in the embodiment of FIGS. 1-7, wherein the body of the valve stem is rigid and an o-ring is provided in its end surface for improved sealing.

In FIG. 9, the one-way outlet valve is shown in the closed position, which means that the pressure inside the socket well has not reached a level above the ambient pressure that caused the valve stem to move outward and open the one-way valve passage. In FIG. 9, the manual valve is in the closed position.

In FIG. 18, the external ramps of the handle portion are shown (the one near the viewer in solid lines and the one hidden from view in dashed lines) and the cooperating bore and internal ramps of the base portion are shown in dashed lines.

FIG. 20 is a front-top perspective view of the valve device of FIG. 19.

FIG. 21 is a rear-top perspective view of the valve device of FIGS. 19 and 20.

FIG. 22 is a left side view of the valve device of FIGS. 19-21, with the right side view being a mirror image.

FIG. 23 is a front view of the valve device of FIGS. 19-22.

FIG. 24 is a rear view of the valve device of FIGS. 19-23.

FIG. 25 is an exploded, front perspective view of the valve device of FIGS. 19-24, with one embodiment of a wrench for taking the valve device apart shown at the lower right of the figure.

FIG. 26 is an exploded, rear perspective view of the valve device of FIGS. 19-25.

FIG. 31 is a cross-sectional view of another embodiment, which comprises a manual valve as in the embodiment of FIGS. 19-30 but does not comprise a one-way valve.

FIG. 32 is a schematic, rear cross-sectional view of the embodiment of FIG. 31, shown with the handle rotated to close the manual valve, the view taken generally along the lines 32-32 in FIG. 31, but without all the cut sections being marked with cross-sectional hatch lines so that the o-ring and circumferentially-extending tab are easier to see.

FIG. 33 is a schematic rear view as in FIG. 32, wherein the handle has been rotated to open the manual valve, as may be seen from the handle bore aligning coaxially with the o-ring and base bore.

FIG. 38 is an exploded, front perspective view of the valve device of FIGS. 34-37.

FIG. 39 is an exploded, rear perspective view of the valve device of FIGS. 34-38.

DESCRIPTION OF CERTAIN EMBODIMENTS OF THE INVENTION

Figure 9:
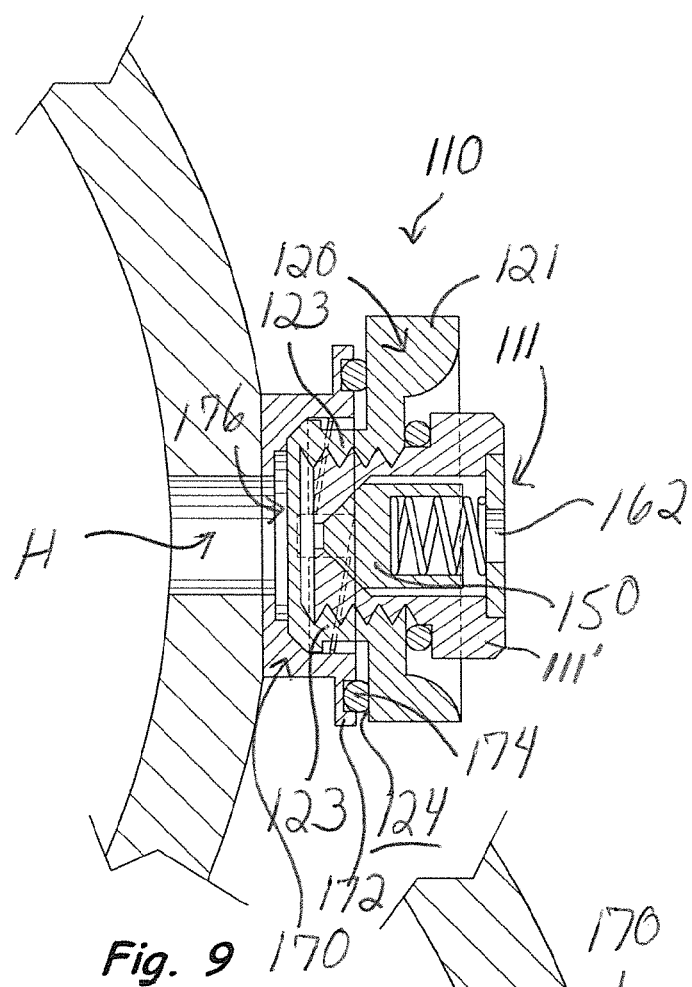
FIG. 9 is a cross-sectional view of an alternative embodiment of valve device, installed on a hard socket exterior surface over a hole, wherein the valve device comprises a one-way outlet valve similar to the embodiment of FIGS. 1-7 and also one embodiment of the invented manual air inlet and outlet valve.
Figure 10:
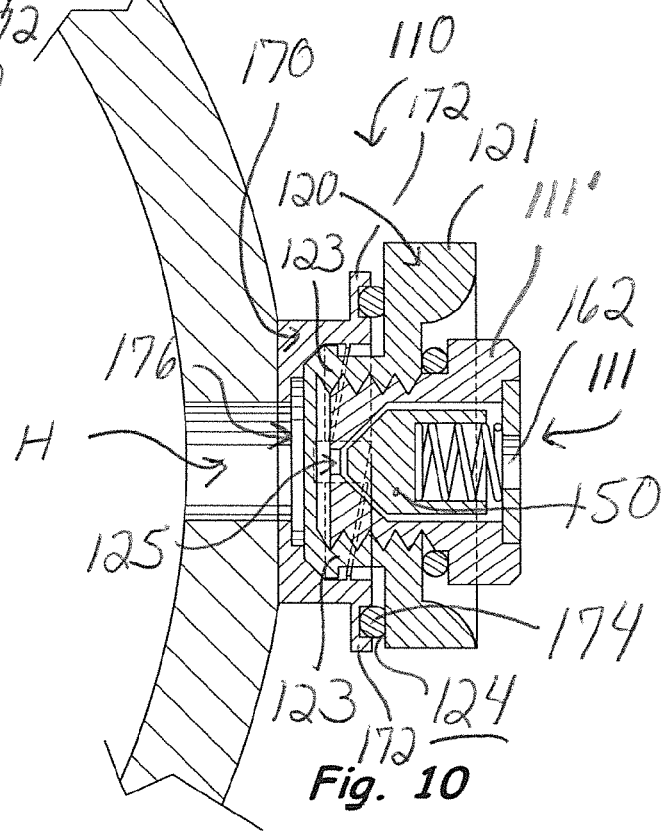
FIG. 10 is a cross-sectional view of the embodiment of FIG. 9, wherein the manual valve is still in the closed position, but the one-way outlet valve has opened to allow expulsion of air from the socket well.
Figure 11:
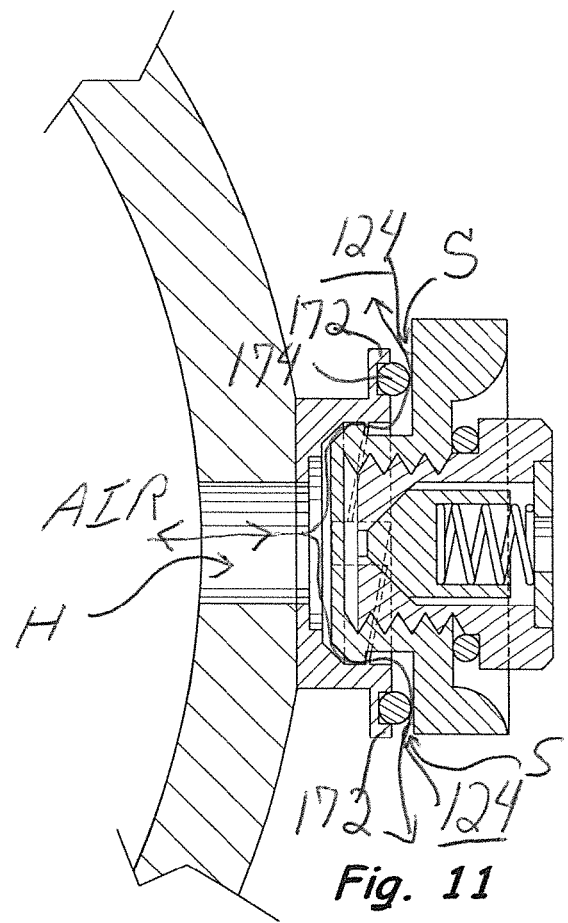
FIG. 11 is a cross-sectional view of the embodiment of FIGS. 9 and 10, wherein the one-way valve is in the closed position, but the manual valve has been opened, by twisting/rotating the handle portion relative to the base portion, so that air may enter or exit the hard socket well from a passageway between said handle portion and said base portion, a portion of which is created by slight distancing of the handle portion from the base portion upon operation of a tab-and-ramp system.
Figure 12:
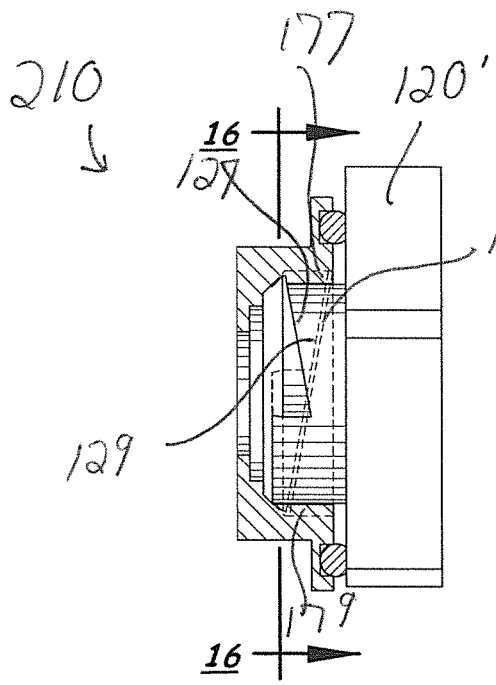
FIG. 12 is a side view of the embodiment of FIGS. 9-11, removed from the hard socket, wherein the base portion is shown in cross-section and the manual valve is shown closed, and the valve housing and one-way valve are not shown for better viewing of the tab-and-ramp system.
Figure 13:
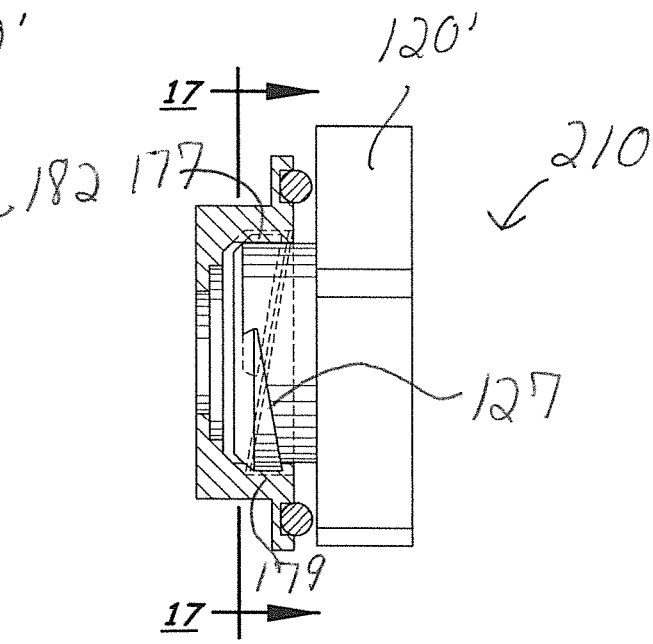
FIG. 13 is a side view of the embodiment of FIGS. 9-12, removed from the hard socket, wherein the base portion is shown in cross-section and the manual valve is opened, and the valve housing and one-way valve are not shown for better viewing of the tab-and-ramp system.
Figure 14:
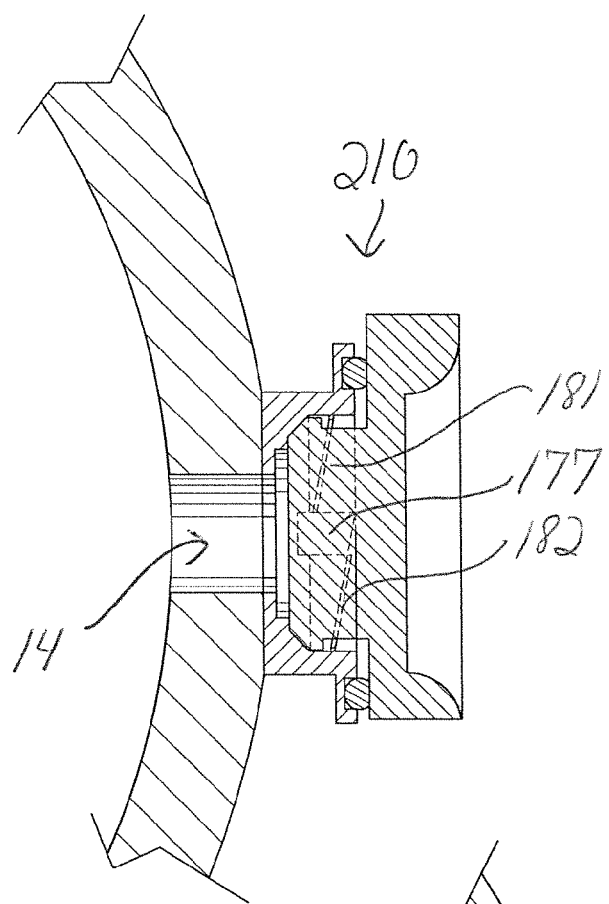
FIG. 14 is a cross-sectional view of an alternative embodiment of the valve device installed on a hard socket wall over a hole, which valve device comprises a manual valve in the closed position and which does not comprise a one-way inlet and outlet valve.
Figure 15:
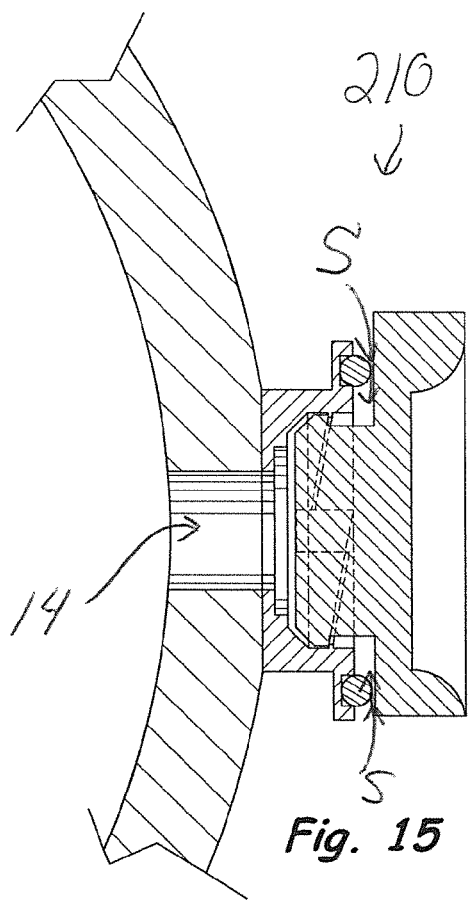
FIG. 15 is a cross-sectional view of the embodiment of FIG. 14, wherein the handle portion has been twisted/rotated to open the manual valve, so that air may enter or exit the hard socket well from a passageway between said handle portion and said base portion.
Figure 16:
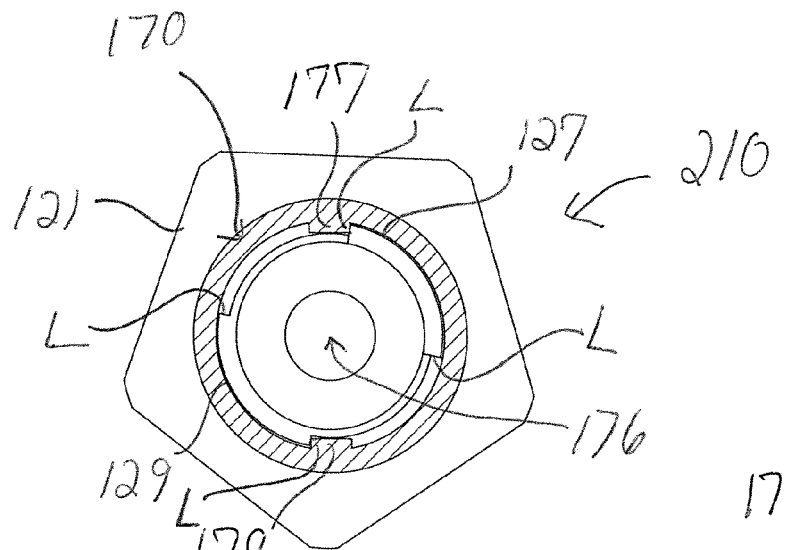
FIG. 16 is a cross-sectional view of the embodiment of FIG. 12, viewed along the line 16-16 in FIG. 12, this cross-section portraying positions of tabs and ramps in a position wherein the manual valve is closed.
Figure 17:
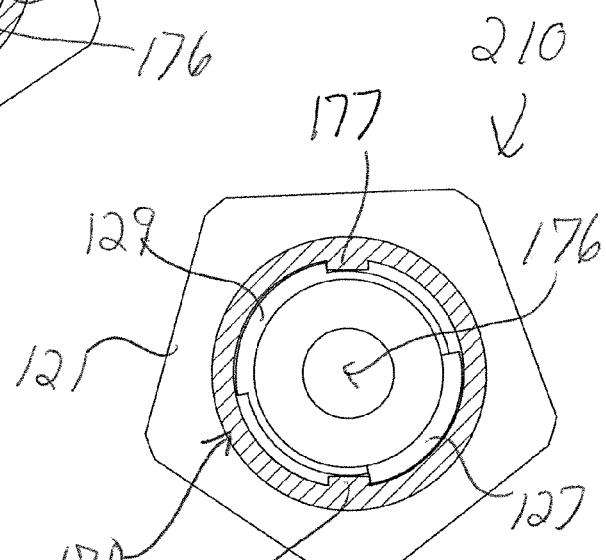
FIG. 17 is a cross-sectional view of the embodiment of FIGS. 12 and 13, viewed along the line 17-17 in FIG. 13, this cross-section portraying positions of tabs and ramps in a position wherein the manual valve is closed.
Figure 18:
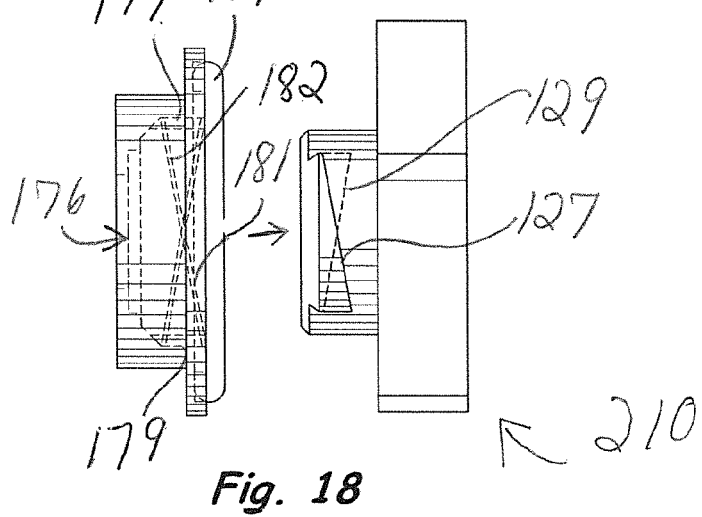
FIG. 18 is a side view of the embodiment of FIGS. 14 and 15, with the handle portion separated from the base portion.

In the Figures, there are shown several, but not the only, embodiments of the valve device for prosthetics. FIGS. 1-8 illustrate one but not the only embodiment having only a one-way air-outlet valve. FIGS. 9-11 illustrate one but not the only embodiment having both a one-way air outlet valve and a two-way-air-flow manual valve. FIGS. 12-18 illustrate one but not the only embodiment that having only a two-way-air-flow manual valve. FIGS. 19-30 illustrate an alternative embodiment having both a one-way air-outlet valve and a two-way-air-flow manual valve. FIGS. 31-33 illustrate an embodiment similar to the valve device of FIGS. 19-30 but without the one-way valve. FIGS. 34-41 illustrate another embodiment of a valve device having both a one-way valve and a manual valve.

As discussed earlier in this document, many of skill in the field of prosthetics still apply the term "suction" to a fit or suspension of the prosthetic to the limb ranging from substantial suction (with a "true" seal, large resistance to equalization of pressure between the inside and the outside of the socket) to slight suction (with a "partial" seal, small resistance to said equalization such as with many popular liners). Therefore, the terms "suction," "suction-fit," and "suction suspension" herein are therefore not limiting to a particular amount of pressure differential, but to the general process known well in this field of providing a "roll-on" liner or other "interference" liner that helps keep a socket on a residual limb while creating at least a small amount of blockage/hindrance to air freely moving in and out of the socket well past the residual limb.

Therefore, it may be said that any amount of negative pressure in the space(s) between the liner-sheathed stump and the interior of the socket, relative to ambient (outside of the socket), may help to hold the prosthesis upon the limb during use. Certainly, more suction is more secure than slight suction, but there may be comfort sacrifices that result from more suction, for example, chaffing or pulling on the limb. A high-suction prosthesis suspension system may cause the user a discomforting disturbance of circulation in the limb on which the prosthesis is worn, due to the build-up of a high degree of partial vacuum during walking, particularly in warm humid weather. Therefore, a very popular conventional roll-on liner is one such as the Ohio Willow Wood Alpha™ liner, which has multiple layers, that is, a rubbery/gel-like inner layer and a thin fabric outer layer bonded to the inner layer, so as to moderate the suction to a reasonably effective amount without allowing the great forces on the limb that can result from a high amount of suction. A "suction liner" or "roll-on liner" suspension, even in moderate range of suction provided by the preferred liners, gives the patient the ability to better control the prosthesis and provides for useful sensory or proprioceptive feedback. This is because there is a more intimate connection between the limb and the prosthetic, over much of the surface area of the limb, compared to old-fashioned waist belts, distal locks, or other methods. Suction or roll-on liner suspension also makes a prosthesis feel lighter as compared to other forms of suspension.

The valve devices described herein aim at improving control of the pressure inside the well of the hard socket, by one or both of one-way air expulsion from the well and manually-controlled two-way air flow in/out of the well. Referring to embodiments that include a one-way air outlet valve, it will be understood by one of skill in the art after reading this application and viewing the drawings, that, once the air pressure inside the hard socket (relative to the ambient pressure outside the socket) exceeds the crack pressure of the one-way valve, the invented one-way or "check" valve opens and air is expelled out through the valve. This is useful during donning of the socket, as the insertion of the limb, or liner-covered limb, increases pressure in the socket well; the one-way valve opens to generally equalize the ambient pressure and the pressure inside the socket in order to allow the donning.

After donning, when the wearer takes each step, pressure is exerted downward on the limb, that is, toward the bottom of the socket well, and this also increases the pressure inside the socket well. Again, the preferred one-way valve will "crack" or "pop" to relieve this pressure, and then close when the pressure is generally equalized by cessation of the downward pressure of the step, and/or when the swing phase of the gait suspends the prosthetic from the residual limb/liner and a slight suction/vacuum (relative to the ambient pressure) tends to be created in the socket. Certain embodiments of the valve are designed with a "crack pressure" (or "set-point") in the range of less than or equal to 3 psi differential, and preferably 1-3 psi, or more preferably 1-2 psi, differential. Therefore, with a pressure inside the socket well ranging from suction/ vacuum (less than ambient) up to but not including the set-point (slightly higher than ambient), the valve will remain closed to not allow air to flow through the one-way valve, that is, neither out of the socket or into the socket through the one-way valve. When the pressure inside the socket well reaches the set-point, the one-way valve will only to allow air flow out of the socket well until the pressure differential has fallen below the set-point, that is, until the "extra" pressure inside the socket well is relieved. Then, typically, the subsequent swing portion of the gait reduced the pressure in the well to slightly below ambient, thus, qualifying the suspension overall as "partial suction".

Figure 1:
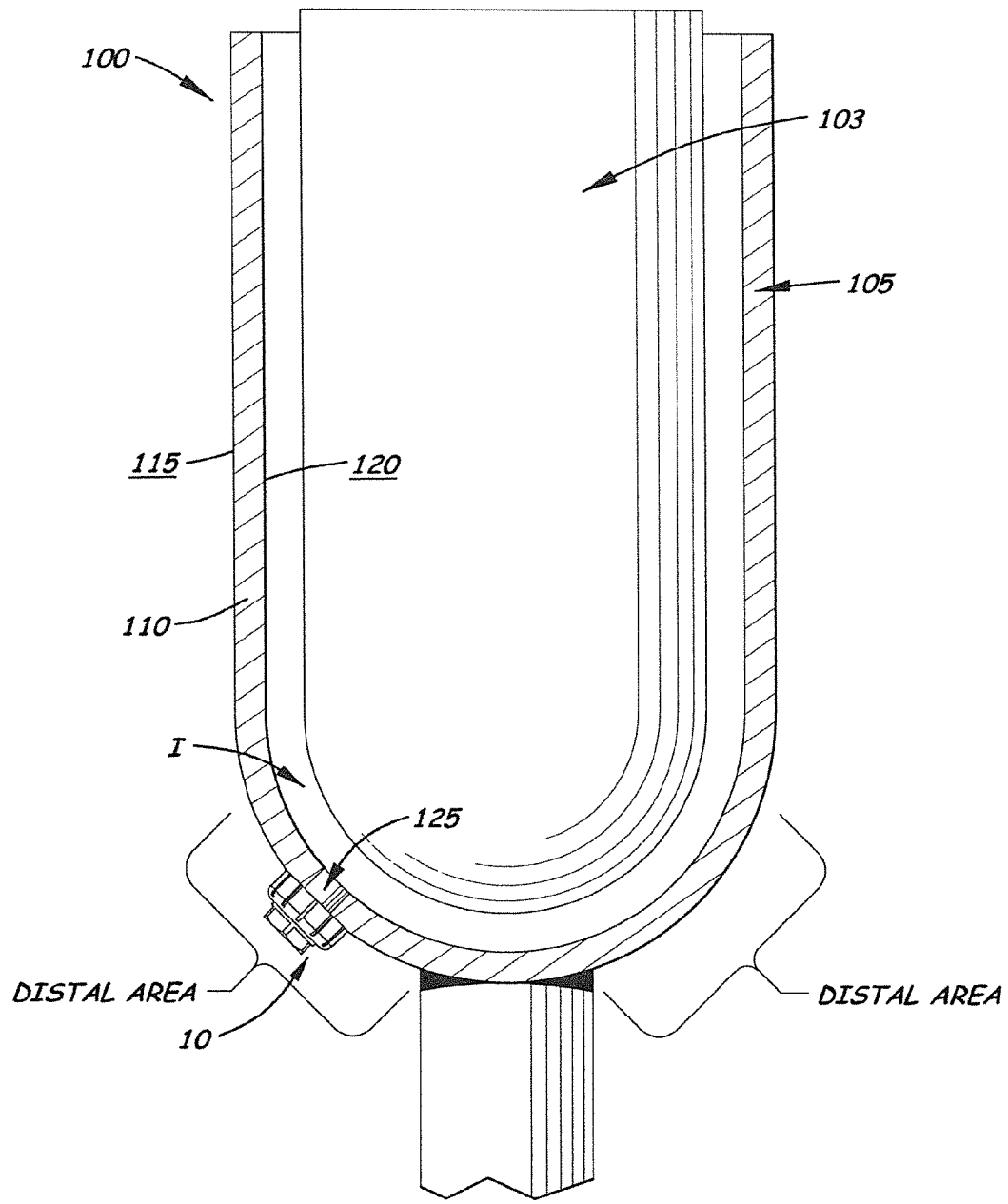
FIG. 1 is a schematic view of a hard socket and liner combination, wherein one embodiment of the valve device is shown attached to the outside of the hard socket. The liner is shown as spaced from the socket, but it will be understood from the foregoing discussion that the liner and socket will tend to be in close contact for at least part of the length along the socket and preferably all around the circumference of the liner and socket at or near the top (proximal region) of the socket. Some space between the liner-covered limb distal end and the socket interior surface distal end is normally present, so that the limb does not reach all the way to the distal end of the well of the socket.

Valve device 10 is adapted to cooperate with a suspension system 100 for external prosthetic devices, which, as discussed in the Related Art section, preferably include a liner that provides at least some blockage/hindrance to air passing between the socket and the liner. As shown in FIG. 1, suspension system 100 comprises a liner 103 received on a residual limb, and a hard socket 105 adapted to fit over the liner 103 and residual limb. The hard socket 105 comprises a sidewall 110 defining an interior space I, wherein the sidewall 110 comprises an outer surface 115 and an inner surface 120. The hard socket may be chosen from many conventional rigid prosthetic sockets currently available on the market. The suspension and/or connection systems for connection the hard socket may include locks, straps, and other mechanisms that are available on the market.

The liner 103 is preferably a roll-on liner, and may be of various types, as discussed in the Related Art section, which provide varying amounts of "suction." Modern liners comprising both an inner gel layer and a textile/fabric outer layer are preferred, and the preferred valve devices of the invention cooperate well with these liners. Therefore, an object of the valve devices comprising a one-way air outlet valve is to allow air to be expelled quietly and consistently, even as often as every step, as may be desired with the amounts of air "leakage" experienced with fabric-covered liners.

As shown in FIGS. 2-7, valve device 10 comprises a base 20 having an internally threaded circular bore 22 extending through the base 20. The base 20 is generally cylindrical in shape and is preferably fabricated from a durable polymeric material or "plastic." Alternatively, the base 20 may not comprise threads, but may instead have other adaptation for joining to the one-way valve assembly that is inserted and secured to the base. For example, a bayonet or other latching mechanism that anchors or secures the one-way valve assembly into the base may be used.

Figures 1B, 1C:
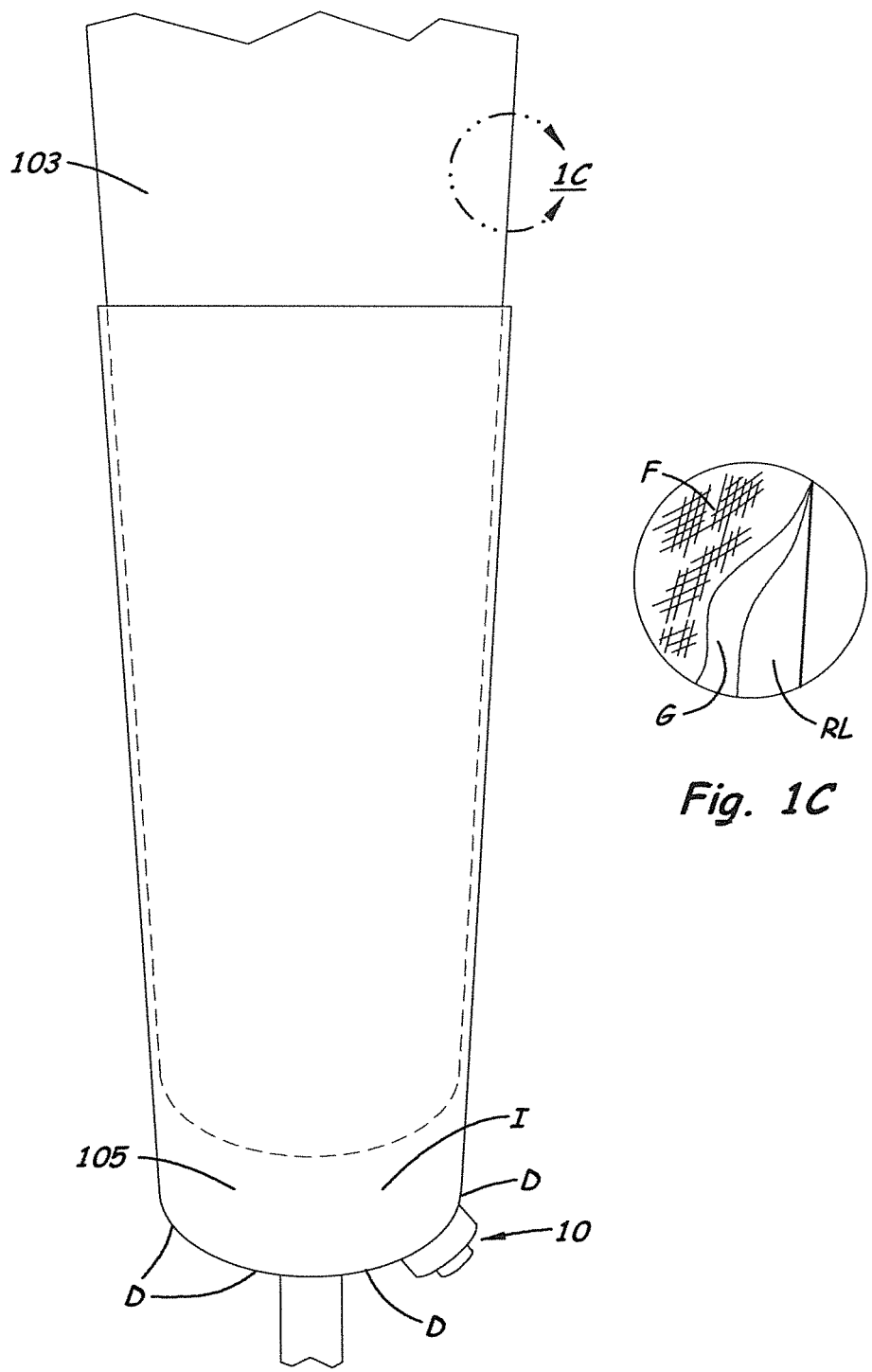
FIG. 1B is a schematic view of a hard socket holding a residual limb with second generation roll-on liner, with one embodiment of the valve device installed on the hard socket distal portion. This view illustrates more accurately the preferred relationship of residual limb, roll-on liner, and socket.
FIG. 1C is a schematic cross-section detail view of a two-layer liner on a residual limb RL, such as in FIG. 1B, wherein the liner has an inner gel-layer G that contacts the residual limb RL and an outer fabric layer F that adhered to the gel-layer G.
Figure 2:
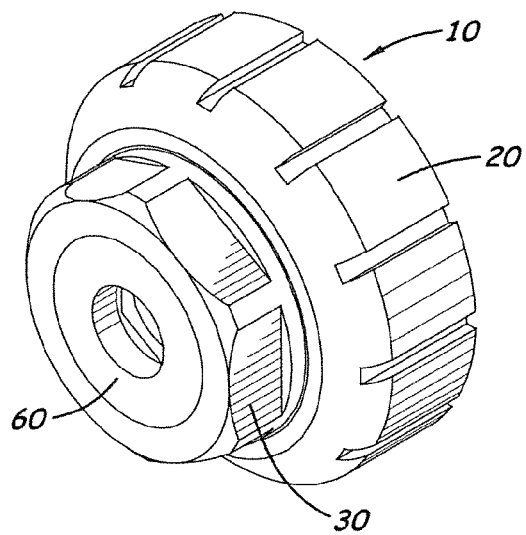
FIG. 2 is a front perspective view of the valve embodiment of FIG. 1, which valve embodiment comprises a one-way air outlet valve but not a manual air inlet and outlet valve.
Figure 3:
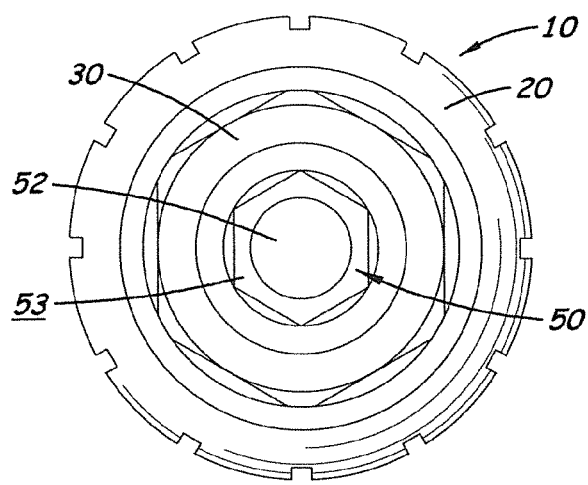
FIG. 3 is a front view of the valve embodiment shown in FIGS. 1 and 2, with a front cover, o-ring/gasket, and spring removed to better show internals of the valve.
Figure 4:
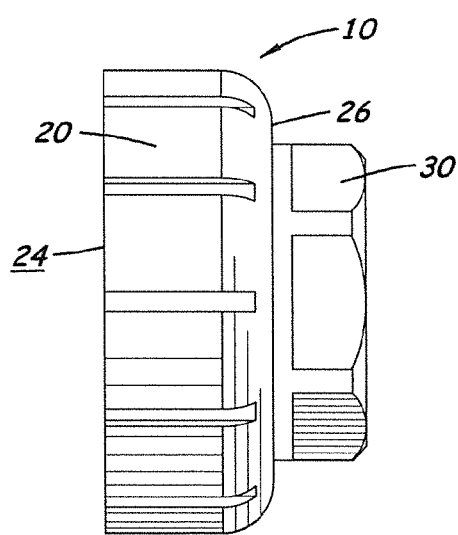
FIG. 4 is a side view of the valve embodiment shown in FIGS. 1-3.
Figure 5:
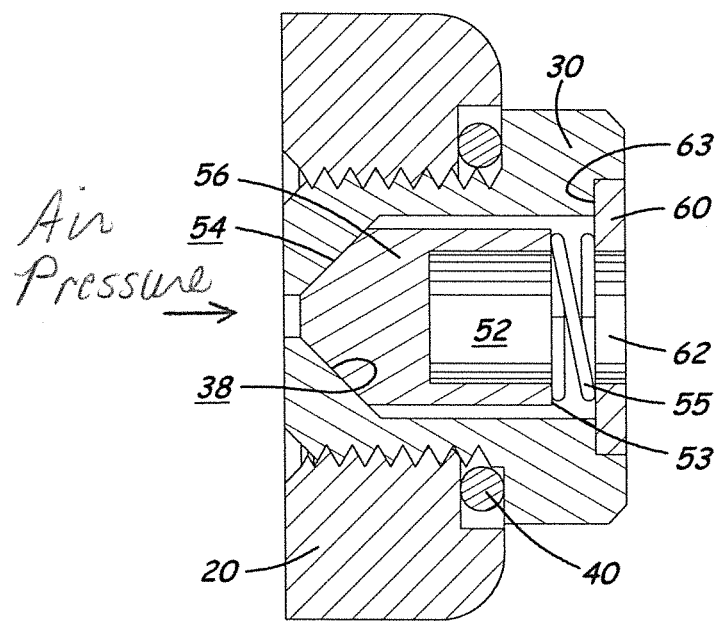
FIG. 5 is a cross-sectional side view of the embodiment shown in FIGS. 1-4, showing the valve in the closed position.
Figure 6:
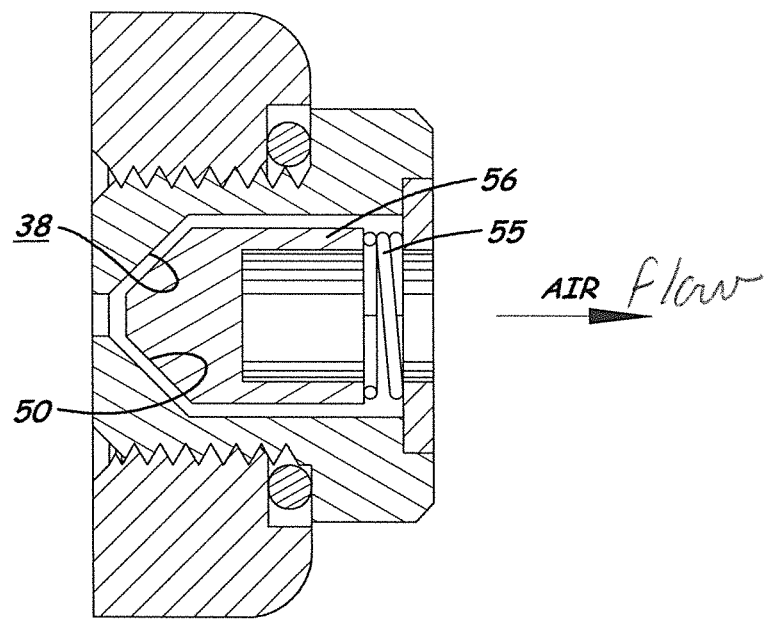
FIG. 6 is a cross-sectional side view of the embodiment shown in FIGS. 1-5, wherein the valve is shown in the open position allowing air to be expelled.

The base 20 has a generally flat bottom portion 24 and a slightly curved or rounded top portion 26 (see FIG. 4). The bottom 24 of the base 20 may be slightly concave to mimic the contour of the outer surface 115 of the socket in the preferred distal installation area on the socket. See FIGS. 1 and 1B, wherein the region labeled as "Distal Area" (or D) is indicative of the preferred, but not the only, region for attachment of the valve device. Distal attachment is preferred, wherein "distal" broadly refers to attachment of the valve device to the socket in a region below where the lower-most end of the residual limb will reach in the socket during use. Distal attachment of the valve device, however, preferably does not include attachment of the valve device at the bottom-most point of the socket, as this location is occupied by the post leading to the prosthetic foot and/or a distal lock that connects to the lower-most end of the residual limb.

With the valve device 10 placed on a distal area of the hard socket 105, it may expel air as needed even when the residual limb is nearly fully, or fully, inserted into the socket. Also, in this area, the valve device 10 is discreet when covered by clothing and does not protrude to an extent causing it to catch on clothing or other items, as it would from a more proximal side of the socket Thus, valve device 10 and attachment of the valve device may be used effectively with modern thin-walled, lightweight sockets. In certain embodiments, after the base 20 is attached to the outside surface 115 of the hard socket 105, preferably by adhesive(s) known in the field of prosthetic sockets, a hole 125 is drilled through the sidewall 110 of the hard socket 105 via the bore 22 in the base 20, so that the hole 125 generally aligns with the interior bore 22, and bore 32 and opening 62 discussed below, for fluid communication between the socket well, hole 125, bores 22, 32 and opening 62 to vent air out of the socket interior I. The opening/hole 125 in the socket wall is made by drilling or otherwise cutting through the socket wall, and this step preferably does not include any threading or other shaping or preparing of the socket or the hole therein. In certain alternative embodiments, the valve device may extend into the socket wall but not into the interior space I of the hard socket 105, for example, not so far as to break the plane of the inside surface 120 of the hard socket 105. Such as embodiment is portrayed in FIG. 19, wherein a hole is pre-forming in the socket, adhesive is applied to the sidewalls of the base and/or the wall defining the hole in the socket, and the valve base is inserted preferably part way into the socket wall. Still, one may see in FIG. 19 that is it preferred for the valve device not to reach or pass the plane of the inner surface of the socket wall.

One may see from the drawings that valve device 10 has base 20, o-ring 40, valve housing 30, stem 50 and ring/cover 60 all being coaxial, creating a passageway or "exit path" for air to pass through when the one-way valve opens. Note that, when fully assembled, the ring/cover 60 may snap into housing 30 (so that it can be easily removed for cleaning of the system) or may be attached to housing 30 by other methods such as adhesive.

In use, when the air pressure inside the hard socket 105 (between the liner-covered residual limb and the socket interior surface) exceeds the desired air pressure, as further discussed below, the air will force the valve stem 50 to move away from the opening 125 in the hard socket 105, compressing the spring 55 against the ring 60. This movement of the stem 50 unseats the end 54 of the stem from the sealing surface 38, allowing air to flow around the end 54 and along the sides of the stem to the opening 62 of the ring, and out to the ambient air.

In other words, the valve device 10 comprises the valve assembly 11 that is inserted into the base 20, which valve assembly 11 comprises a valve housing 30 having an internal circular bore 32 with a conical sealing surface 38 and an external threaded portion 34. The threaded portion 34 on the valve housing 30 has a slightly smaller diameter than the threaded bore 22 in the base 20, so that it may cooperate with the threaded bore 22 in the base 20. As explained above for the base 20, the valve housing 30 may be otherwise adapted for connecting/securing to the base. For example, the valve housing may not have any threads and may instead have bayonets that are received in slots in the base when the valve housing is inserted into and rotated in the base.

The exterior of the valve housing 30 is shown as "hex-shaped," but other shapes may be used, such as other polygonal shapes or a cylindrical shape. The hex-shape may allow the technician to easily install and tighten the valve housing or the entire assembly in the base. Also, because the hex-shape provides a good surface to grip, it may allow the user to manually open the valve, in effect by disassembling the valve (removing the valve assembly from the base), if necessary, prior to the user removing his/her residual limb from the hard socket 105.

An o-ring 40 or other seal is placed in a recess in the base 20 between the base 20 and the valve housing 30. Once the valve housing 30 is threadably or otherwise received and secured in the base 20, an air tight seal is created between the base 20 and the housing 30.

The valve assembly 11 further comprises a valve stem 50 received in the bore 32 of the housing 30. The valve stem 50 slides axially inside the bore 32 to seat against the sealing surface 38 of the housing, when the valve is closed, and to move away and unseat from the sealing surface 38 when the valve is open. A spring 55 biases the valve stem 50 into the closed, seated position to close the valve except when a differential air pressure overcomes the spring 55 bias and pushes the valve stem 50 away from the sealing surface. Spring 55, for example, may be a cylindrical coil compression spring, the design of which is the main determining factor in the crack pressure of the valve and which one of average skill can design after reading this disclosure.

The valve assembly, including the bias spring 55, are adapted so that a differential pressure selected from a certain amount will "crack" or "pop" open the valve. In other words, the valve assembly and particularly the spring 55 are preferably designed so that, when the pressure on the "inner side" of the valve (to the left in FIGS. 5 and 6, and typically on the inside of the socket between the liner-covered limb and the interior surface of the socket at the lower end of the socket) is a certain amount (for example, 1-3 psi or 1-2 psi) above the pressure on the "outer side" of the valve (to the right in FIGS. 5 and 6, and typically outside the socket), then the valve will open. As soon as the differential pressure drops (that is, as soon as the inner pressure is less than the certain amount, the spring 55 will again bias the valve stem 50 to the closed, seated position. Thus, as discussed above, the valve will open, if necessary, with each step of the wearer's gait, to allow air to vent from the socket well, and then quickly close after the air has been vented and/or when the swing portion of the gait lowers the pressure inside the socket well.

The valve stem 50 may have an internal bore 52 (or other hollow or recessed end or cavity that opens to the housing bore preferably at the spring-end of the valve) that may receive air that is flowing out of the valve in the "exit path" comprising passing around the stem, through or around the spring, and out through the outer end of the valve (at ring 60). Internal bore 52 may provide extra space for this flowing air, as it passes around or through the spring to exit the valve, thus helping prevent unpleasant noise or venting sounds that might occur with too-narrow portions of the exit path. Further, various embodiments of the bore 52 may be advantageous during the molding or machining process, for weight reduction, and/or for cooperating with or connecting to a spring or other bias member. The preferred location of the spring 55 is between the flat face 53 of the valve stem 50 and the inner face 63 of the ring 60, and held there securely enough that it may be repeatedly compressed between those surfaces and then released, when the valve opens and closes, respectively, without significantly shifting from its preferred radially-centered position.

Further, as shown in FIG. 8, there may be an o-ring 58 or other material on the generally conical end 54 of the stem 50, which o-ring 58 or other material is preferably a softer or more flexible material, compared to the preferred brass or hard plastic valve stem 50, for enhancing the seal between the stem 50 and the sealing surface 38. Alternatively, the entire stem 50, the conical end 54 of the stem, or another portion of the stem may be made of a softer plastic or other material with enhanced sealing performance.

Retaining ring 60 is a generally thin disc that is friction-fit, snapped, or otherwise secured and anchored into the bore 32 of the housing 30 to retain the spring 55 and the stem 50 in their proper positions inside the housing. The ring 60 is preferably secured to the housing, on ledge 39, in such a way that it will not normally come out of the housing, but that an external prosthesis technician could pry or otherwise remove it to clean the valve assembly 11 and/or replace parts of the valve assembly 11. Ring 60 has an opening 62 through which the air is expelled. Alternative ways of retaining the valve stem, spring, and/or other parts as may be desired, in the housings of the valve may be used.

Stem 50 is a hexagonal, or other polygonal shape, so that it has multiple flat or generally flat sides 56. Therefore, the air may flow along the end 54 of the stem and through the bore 32 of the housing in between the housing inner surface and one or more of the flat sides 56. This provides multiple passages for the air, with each preferably being a relatively wide passage (that is, radially wider than if the stem where cylindrical inside a cylindrical housing bore), which is believed to be important for reducing air-venting noise. These passages may be said to be "spaced gaps" between the stem and the housing, in that they are spaced apart (separated) by the edges 57 of the stem, which contact, or come very close to, contacting the bore 32 surface. These gaps, therefore, may also be called non-annular gaps or non-annular spaces, as the gap/space between the stem and the bore of the housing is preferably not simply a continuous, annular space around the entire stem, but rather multiple axial passageways that are separated/spaced apart by the edges 57 that are close to, or that contact, the bore 32. It may also be said that, because the stem and the housing bore are not the same shape (and particularly not the same circumferential shape), there are multiple gaps between the stem and the housing bore created by this difference in shape. This also places the stem 50 in the housing in a slidable arrangement, where it slides axially in the housing bore 32, with contact being between the edges 57 of the sides 56 and the bore 32 surface, but not all the way around the circumference of the stem.

The base 20, valve housing 30, and retaining ring 60 may be fabricated, for example, from a light-weight durable material, for example, Delrin™ plastic; however, other materials may be used such as aluminum, titanium, nylon or other plastics. Additionally, the stem 50 may be hard plastic or brass, but also may be manufactured from other materials, for example, including other metals, plastics, or combinations thereof.

Referred now to FIGS. 9-11, an alternative embodiment comprises a valve device 110 that includes a manual valve as well as a one-way valve. From the cross-sectional view of FIGS. 9 and 10, one may see that the one-way valve assembly 111 is threadably connected to a handle 120 that generally serves the same purpose relative to the valve assembly 111 as base 20 serves to valve assembly 11, however, handle 120 is not directly attached to the socket. Instead, handle 120 is preferably expanded in its outermost diameter and/or provided with a flared outer circumference portion, or grip portion 121, to provide the user a larger, and preferably easily-rotatable grip surface when operating the manual valve. Further, instead of having a flat bottom (or rear surface) that attaches directly to the hard socket, handle 120 has a rear protrusion 123 that is received in and operatively connected to base 170. It is base 170 that is directly connected to the socket, in certain embodiments, by adhesive in the same way as discussed above for the base 20. As discussed in detail for base 20, base 170 preferably does not connect to, or include, any structure that reaches through the socket wall or into the socket well, but rather firmly is glued/adhesively attached to a distal region of the socket exterior wall surface. As discussed with base 20, a hole (H in FIGS. 9-11, 14, 15) may be drilled through the socket wall after attachment of the base 170 to the socket, or by other means or steps. Such an attachment will be effective for a thin-walled socket and will be convenient and simple compared to more complex mechanisms that require fasteners or clamps or other structure both on the inside and the outside of the wall.

The operative connection of handle 120 (preferably with its valve assembly 111 including valve casing 111') and the base 170 allow said handle and base to form a manual valve that is substantially or entirely independent of the operation of the one-way valve. Handle 120 is preferably rotatable relative to base 170, and is preferably coaxial with the base 170. Upon rotation, in one direction, the handle 120 move close to the base 170 to seal against the base, and, upon rotation in an opposite direction, the handle 120 moves out away from the base 170 to create a space between the handle and base that allows air flow. In the manual valve closed position, shown in FIGS. 9 and 10, the rear surface 124 of the handle grip portion 121 seals to the front flange 172 of the base 170, most preferably by means of an o-ring or gasket 174 provided in a groove on the flange 172 or otherwise retained on the flange. One may see in FIGS. 9 and 10 that the one-way valve assembly 111 may operate as described above for valve assembly 11 (closed in FIG. 9 and "popped" open in FIG. 10) when the manual valve is closed, that is, when the handle 120 and base 170 are in closed, sealed condition. When the manual valve is closed, the only passageway possible for air exit through the valve device 110 is to pop the one-way valve. It is noteworthy that, when the manual valve is closed, air may pass through the base 170 (through bore 176) and through the rear aperture 125 in the rear protrusion 123 to reach the one-way valve stem 150, and, upon opening the stem 150 (as discussed above for stem 50), the air may flow around the stem and out of the one-way valve assembly via opening 162. When the manual valve is opened, as discussed below, air will flow out via the space/gap between the base 170 and the handle 120, rather than popping the one-way valve, or will flow in via said space/gap, depending upon the relative pressures inside the socket and outside the socket.

The preferred method of operating the manual valve is by rotation of the handle 120 relative to the base 170, wherein cooperating structure of the handle and base serves to distance the handle 120 from the base 170 upon at least a portion of said rotation. Said cooperating structure, in certain embodiments, comprises at least one ramp on either of said handle 120 or said base 170 and at least one riding member on the other of said handle or base, wherein relative rotation of the handle and base allow the riding member to slide or "ride" along the ramp to change the relative axial location of the handle and the base. Said at least one ramp is slanted so that rotation preferably in the range of 30-270 degrees (more preferably 30-90 degrees and most preferably 30-70 degrees) distances the handle from the base enough to unseal the two from each other for air flow there-between. The riding member may be a protrusion or ramp. When the riding member is itself a ramp, one may consider the ramps to cooperate as do threads, but only threads that allow less than a full rotation. In other words, the handle may be unscrewed from the base less than a full rotation, so that the handle movement has an axial component to move the handle slightly out from the base. The rotational operation of the manual valve, in each of the opening direction and the closing direction, preferably is only a partial rotation (30-270 degrees, more preferably, a partial rotation in the range of 30-90 and, most preferably 30-60, degrees). Opening by rotation in the range of about 30-60 degrees, and closing in the opposite direction by rotation the same amount (also in the range of 30-60 degrees) is particularly comfortable and easy to perform, as the user simple "twists" the handle a short distance one way and then the other. The preferred operation, therefore, is more like a quick twist than an screwing/unscrewing a threaded system.

In certain embodiments, two ramps 127, 129 are provided 180 degrees apart on the outer, cylindrical surface 134 of the rear protrusion 123. The ramps 127, 129 are present in FIGS. 9-18, but may be seen to best advantage in FIGS. 12, 13, and 18. Two tabs 177, 179 are provided on the interior cylindrical surface of the bore through base 170, and extending between the tabs 177 179 on said interior surface are ramps 181, 182. When the preferred handle 120 is rotated clockwise relative to the preferred base 170, ramps 181, 182 ride along ramps 127, 129 to pull the handle closer to the base, as if the handle were being screwed into the base, to an extent that seals the handle to the base at o-ring/gasket 174. When handle 120 is rotated counterclockwise relative to the preferred base 170, ramps 181, 182 ride in the opposite direction along ramps 127, 129 to allow the handle to be slightly distanced from the base, as if the handle were being unscrewed part-way from the base, to an extent that unseals the handle from the base at o-ring/gasket 174. In this open condition, as shown in FIG. 11, air may flow out from the socket or into the socket through the space S (space S shown in FIG. 15) between the handle and the base.

Tabs 177, 179 move, during said rotation, preferably between limiting structure (L, FIGS. 16 and 17) that is preferably at the ends of ramps 127, 129. The tabs 177, 179 may move between said limits L in areas of the outer surface 134 that is recessed relative to the areas upon which the ramps 127, 129 are located.

The handle 120 and base 170 are preferably connected and disconnectable by means of a snap system, wherein the handle snaps into the base and then is rotatable relative to the base. In certain embodiments, the handle and base snap together by the handle being positionable relative to the base in a position wherein portions of the ramps 181, 182 and/or tabs 177, 179 snap over slightly-protruding structure on the outer, cylindrical surface 134 to a point wherein the handle is base is held on the handle. Preferably, spaces (significantly wider than the tabs 177, 179) exist between the two ramps 127, 129 on the surface 134 (said relatively recessed areas mentioned above) and, as the two tabs 177, 179 into those recessed spaces, slide, portions of ramps 181, 182 also slide into said spaces and portions of ramps 181, 182 snap over the cooperating ramps 127, 129 on the handle rear protrusion outer surface 134. There may be an optional slight protrusion at the entry of the recessed spaces over which the tabs may snap. When the tabs slide into the recessed spaces and the ramps 181, 182 snap over ramps 127, 129, the base ends up in a position relative to the handle wherein the base is close to, and generally tight against the handle, and the manual valve is therefore closed. In this position, the handle and base have snapped together, and are in position for the ramps to slide along each other to open the manual valve when the handle is twisted counterclockwise relative to the base. If substantial pulling on the handle were conducted, the handle might snap off of the base, this is unlikely to happen unintentionally, as only twisting is necessary, and not pulling or pushing, to open and close the manual valve.

In FIGS. 12-15, and 18, there is shown yet another embodiment 210, wherein the valve device 210 comprises only a manual valve and not a one-way air outlet valve. The valve device 210 may be the same as that described above for FIGS. 9-10, but, instead of the handle having a bore there-through that receives and cooperates with a one-way valve assembly, the handle 120' is closed at its front (toward the right in FIGS. 12-15, and 18). The handle may still have an optional, front, central indent/depression, as portrayed in FIGS. 14 and 15. As in the embodiment of FIGS. 9-11, the embodiments of FIGS. 12-15 and 18 allows air to flow out of, and into, the socket, by flowing axially through a portion of the passageway (the portion in the base) and radially (through the space between the flange of the base and the rear side of the rear protrusion 123 of the handle).

Especially-Preferred Embodiments Comprising a Manual Valve

FIGS. 19-42 illustrate certain embodiments that each comprises a manual two-way valve utilizing alignment of bores in the device to open a two-way air passageway. FIGS. 19-30 portray a valve device 310 comprising both a manual two-way valve and an automatic one-way valve, also called an "expulsion" valve. Valve device 310 comprises coaxial portions that are generally symmetrical around the axis of the device 310. FIGS. 31-33 portray a valve device 410 similar to valve device 310, except not comprising the one-way valve. FIGS. 34-42 portray a valve device 510 comprising both a manual two-way valve and an automatic one-way valve or "expulsion" valve, wherein some portions of the valve device 510 are asymmetrical around the axis of the device to enhance effectiveness of the manual handle operation.

Figure 19:
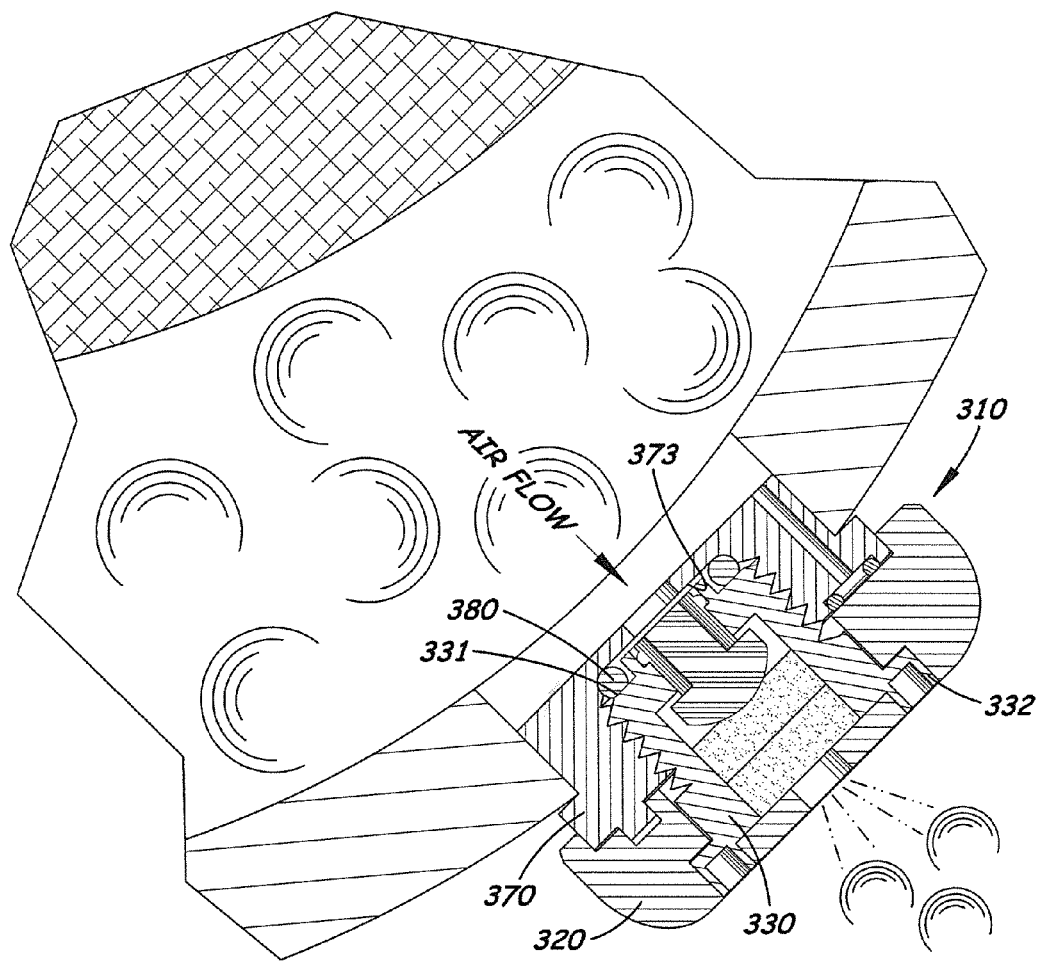
FIG. 19 is a cross-sectional side view of another embodiment of a valve device comprising both a one-way air-outlet valve and a manual air-inlet and -outlet valve, wherein air from inside the socket is shown being expelled through the one-way valve while the manual valve is closed.

As illustrated in FIG. 19, valve device 310 may be installed in a distal region of a hard socket, preferably by pre-forming of a hole through the socket wall, followed by adhesive attachment of the base 370 to the socket so that a portion of the base 370 extends into the hole but not to or past the plane of the inner surface of the socket wall. FIGS. 20-24 show the valve device 310 removed from the socket, from various directions.

As seen to best advantage in FIGS. 25-30, a handle 320 is rotatably connected to the base 370 by rotatably encircling a valve housing 330 that is connected, preferably by threaded connection, to the base 370. The valve housing 330 has an enlarged front end 332 that captures the handle 320 to allow handle rotation while preventing the handle 320 from moving away any significant extent from the base 370. An o-ring 380 or other air-seal is provided between a rear shoulder 331 of the valve housing 330 and the base interior shelf 373.

A circumferentially-extending tab 372 protrudes forward from the front face 371 of the base 370, and is received in a circumferentially-extending channel 322 in the rear surface 321 of the handle 320. The handle 320, held close to the base front surface 371 by virtue of being captured between the base 370 and the valve housing 330, may rotate on its axis (also, the "axis of the device") to an extent allowed by the end surfaces of the tab 372 abutting into the end surfaces of the channel 322. The handle 320 and the base front surface 371 may be said to be generally planar, parallel, and coaxial, with rotation of one relative to the other comprising relative rotation in adjacent parallel planes. The relative lengths of the tab 372 and channel 322 in this embodiment will allow handle rotation of about 80 degrees, while in certain embodiments the rotation may be other amounts, for example, an amount in the range of 30-180, but more preferably in the range of 30-90 degrees. Thus, the preferred manual operation, as discussed above for other embodiments, is a "twist" motion a short distance in one direction to open the manual valve and then the same short "twist" in the reverse direction to close the manual valve.

Twisting the handle 320 to the open position aligns bore 324 in the handle with the bore 374 in the base 370. "Aligning" the bores may include, in this description and the claims, coaxial alignment, generally-coaxial alignment, or other close proximity so that one bore fluidly communicates with the other. Both bores 324, 374 are axial, that is, extending front to rear through the handle and base, respectively, and both are open-ended. The bore 374 of the base is open at the rear surface of the base and so is open to the well of the socket. The bore 324 of the handle is open at the front of the handle in a region exposed at the front of the valve device 310 and so is open to the atmosphere outside the socket and outside the valve device 310. This way, when bores 324, 374 are aligned, air may flow from the socket well, through the device, to the outside, and vice versa from the outside, through the device, and into the socket well. This way, the manual valve can be used for air flow out of the socket, for example for donning, and air flow into the socket, for example for doffing the prosthetic.

An o-ring 381 or another air-seal is provided at the front end of the base bore 374 to seal against the rear surface 321 of the handle. This way, when the manual valve is closed, as in FIGS. 19 and 27, bores 324, 374 are not coaxially aligned and the o-ring 381 seals against the handle rear surface 321 to block the bore 374 and prevent air flowing through the bore 374 in either direction. This way, ambient air cannot enter the bore 374 and flow into the well to disrupt the partial suction suspension. When the handle is turned ("twisted") to coaxially align the bores 324, 374 as in FIG. 28, air flows through the axial passageway created by the aligned bores, including flowing axially past the o-ring 381. In both the closed and open positions of the manual valve, the o-ring 381 prevents air from flowing radially between the handle rear surface 321 and the base front surface 371. Thus, the manual valve involves substantially or entirely axial air flow through the valve device 310, rather than radial air flow.

Inside the valve housing 330 of valve device 310 are provided components of the automatic one-way valve. A cover 360 is snapped into the front end of the valve housing to hold the one-way valve components in place inside the central bore 334.

A elastic umbrella valve member 336, or other flexible and resilient valve member, is provided in the central-bore 334 of the valve housing 330. This umbrella valve 336 comprises a cap 337, and a stem 338 with axial scallops/indentations 338' and a lip(s) at or near the rear end of the stem. The axial scallops/indentations 338' encourage air flow past the valve 336 when the cap is in the unsealed position. The lip(s) are an example of an adaptation to retain(s) the rear end of the stem in place in the valve housing, both when the valve is closed and when pressure pushes the valve forward. For example, the lip(s) may be flared radially outward to be received or abut against a shelf, groove, or other recess in the valve housing (FIGS. 27-30) or, alternatively, to engage the rear-most end of the valve housing (see FIG. 40). With the rear end of the stem retained/restrained in place, the non-restrained portion may stretch or flex forward to unseal the cap from the valve housing. After the air expulsion, with the rear end of the stem still retained in place, the elasticity of the umbrella valve returns the unrestrained portion to its normal position, with the cap sealed against the valve housing.

In certain embodiments, at least one pad 339 or screen, for sound-dampening and/or filtering, is provided in front of the cap 337. In certain embodiments, at least one pad or screen is also provided at the rear of the stem for sound-dampening and/or filtering, for example, between the rear-most end 331' of the valve housing 330 and the interior shelf 373 of the base.

FIG. 25 portrays a wrench 390 for tightening and loosening the valve housing in the base 370. The two prongs 392 protruding from the wrench may be inserted into two diametrically-opposed recesses 333 in the front surface of the valve housing 330, and the wrench 390 may be turned to rotate the valve housing 330 relative to the base 370. This may be especially useful in removing the one-way valve from the valve device 310 for cleaning or replacement of one or more of the components.

Figure 27:
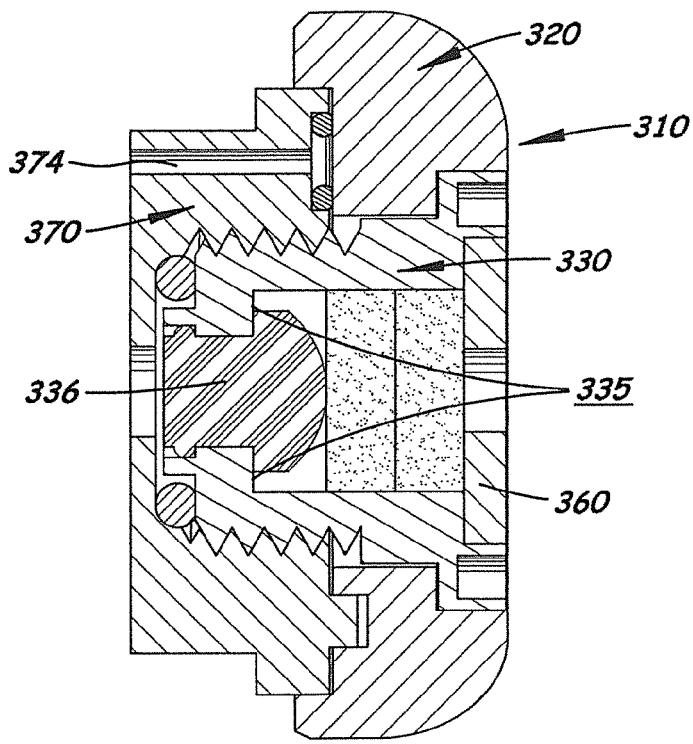
FIG. 27 is a cross-sectional side view of the valve device of FIGS. 19-26, wherein both the one-way valve and manual valve are closed.
Figure 28:
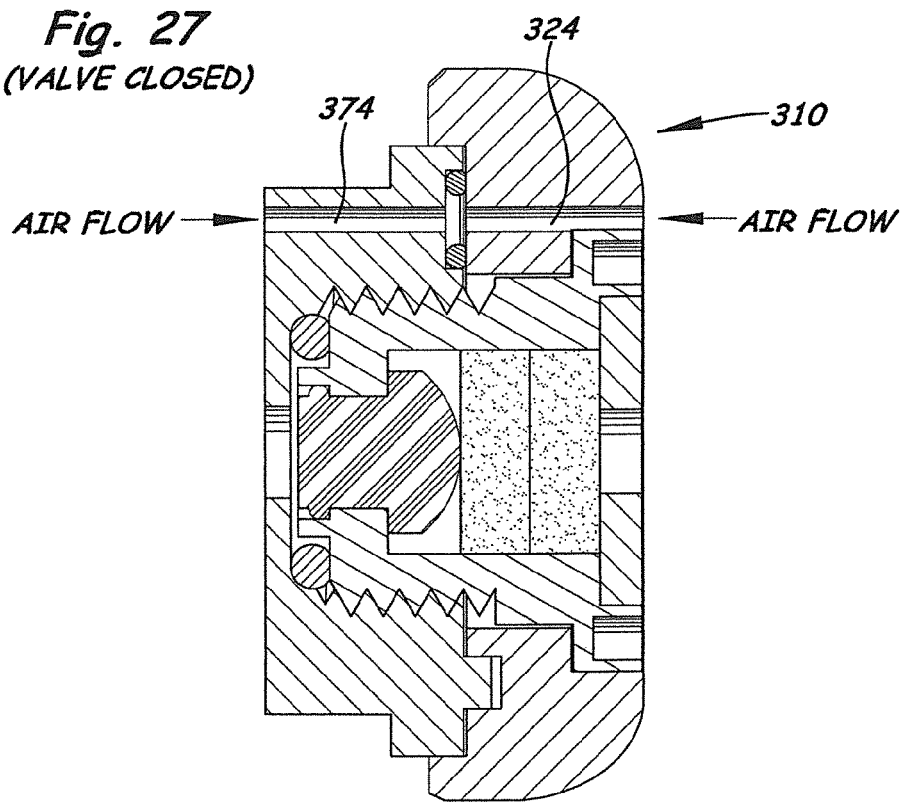
FIG. 28 is a cross-sectional side view of the valve device of FIGS. 19-27, wherein the one-way valve is closed and the manual valve is open, with two arrows showing that air can flow in either direction depending upon the differential between socket well and ambient air pressures.
Figure 29:
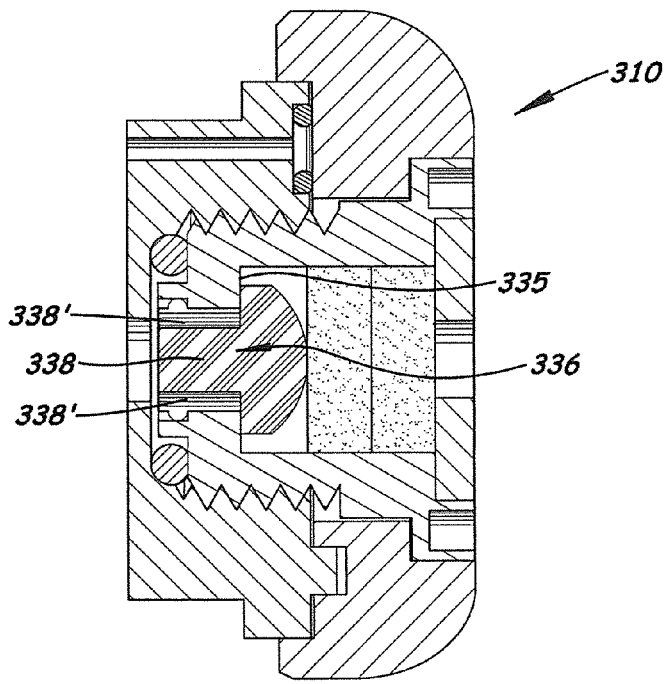
FIG. 29 is a cross-sectional side view of the valve device of FIGS. 19-28, wherein the one-way valve is closed and the manual valve is closed.

At certain times, both the manual valve and the one-way valve are closed, as shown in FIGS. 27 and 29. At other times, the manual valve is opened by the user, as shown in FIG. 28, so that air may flow through the valve device 310 as needed due to donning or doffing for example. Opening the valve preferably comprises twisting the handle to a position that aligns the bores, as discussed above, with the amount of twist guided or limited by mechanical structure on the handle and/or base. For example, the amount of handle rotation may be limited by one or more stop surfaces.

Figure 30:
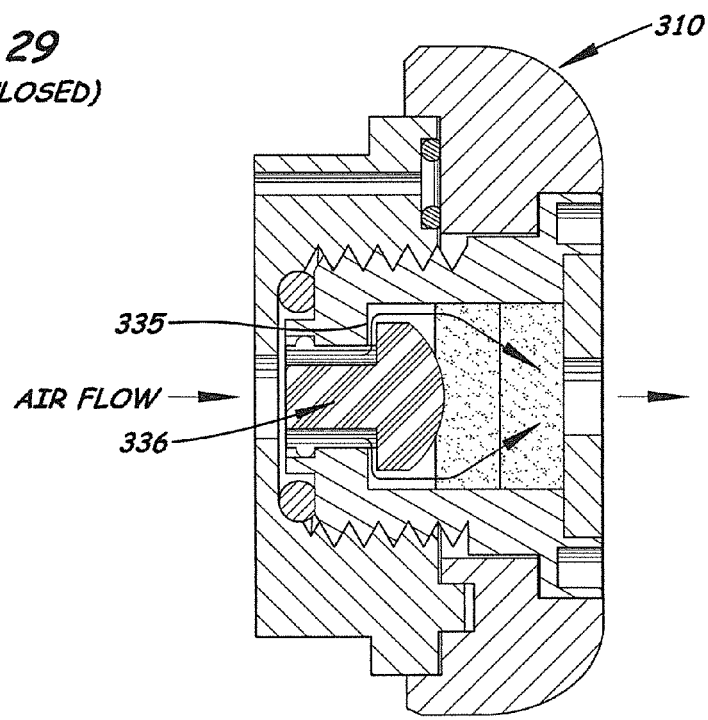
FIG. 30 is a cross-sectional side view of the valve device of FIGS. 19-29, wherein the one-way valve is open and the manual valve is closed.
Figure 34:
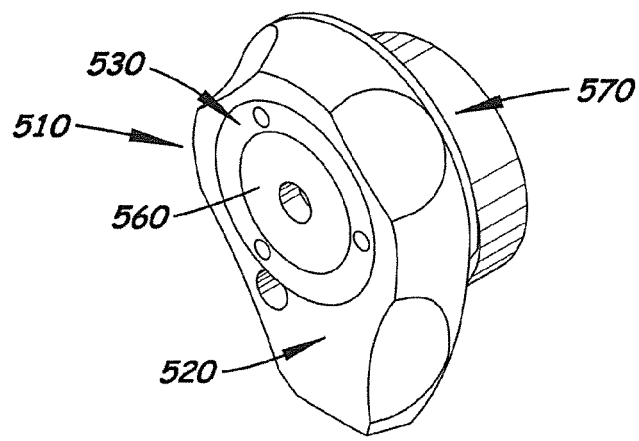
FIG. 34 is a front-top perspective view of another embodiment of a valve device having both a one-way valve and a manual valve.
Figures 35, 36:
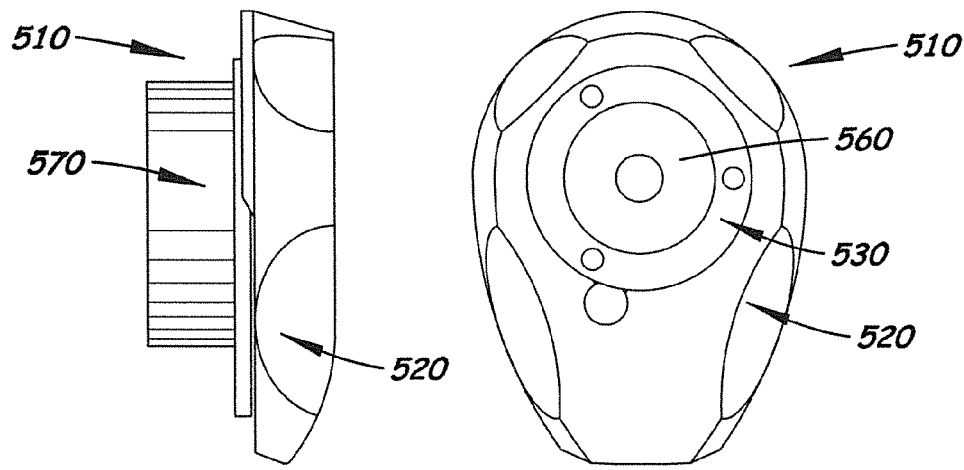
FIG. 35 is a left side view of the valve device of FIG. 34, wherein the right side view is a mirror image.
FIG. 36 is a front view of the valve device of FIGS. 34 and 35.
Figure 37:
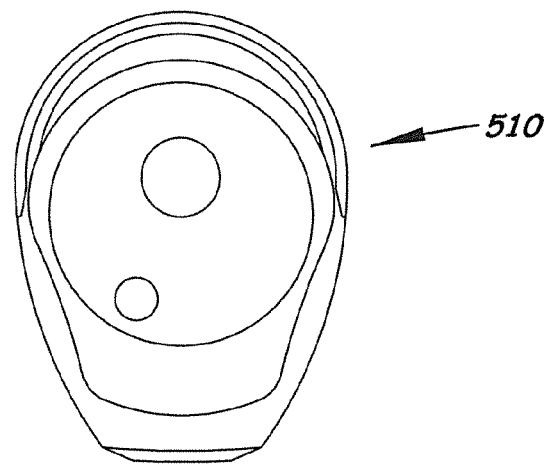
FIG. 37 is a rear view of the valve device of FIGS. 34-36.

When the manual valve is closed and the pressure in the socket well is close to or below the pressure outside the prosthetic, the one-way valve will also be closed, as in FIG. 29. However, pressure in the well frequently builds, due to donning of the socket or the normal gate of the wearer as described earlier, and when the pressure reaches the set-point, the pressure will be relieved by popping of the one-way valve, as also described earlier and as shown in FIG. 30. As discussed earlier, the set-point may be, for example, in the range of less than or equal to 3 psi differential, and preferably 1-3 psi, or more preferably 1-2 psi, differential. The umbrella valve 336 may unseat (unseal) by various mechanisms, for example, with the rear end of the stem retained in position in the valve housing, the stem 338 may stretch slightly forward to move the cap 337 forward slightly away from the valve housing interior shelf 335. Alternatively or in addition, the perimeter of the cap 337 may flex slightly forward away from the interior shelf 335. This stretching and/or flexing allows air to flow through stem scallops 338' and around the perimeter of the cap 337, to continue through the central bore 334 and out through the aperture of the cover 360 (FIG. 30). As soon as a volume of air has escaped that is sufficient to reduce the socket well pressure to below the popping pressure, the stem and cap return to their normal position, due to the resilience of the umbrella valve 336, resealing the one-way valve.

The umbrella valve 336 has been found very effective for the repeated and accurate popping required in normal use of the prosthetic. Due to its stretching or flexing action, and its natural resilience, the valve 336 is unlikely to bind-up on the wall of the bore to become stuck open or stuck closed. The umbrella valve 336 is capable of quickly popping and quickly resealing, and has been found to be durable and unlikely to bind-up or malfunction. Providing pads for sound-dampening and/or filtering, or screens for filtering, further enhances the durability and reliability of the umbrella valve 336 by limiting/preventing grit or other substances from interfering with quick unsealing and resealing of the umbrella cap 337 against the valve housing interior shelf 335 (see FIGS. 27, 29, and 30).

FIG. 31 portrays a valve device 410 similar to device 310, except that the one-way valve has been eliminated. Axle member 430 is a solid piece without a central bore for housing valve components. Axle member 430 retains certain functions described for valve housing 330, for example, it is removably connected and sealed to the base at threaded connection 440 and o-ring 442, it rotatably receives the handle encircling around its middle region 446, and its enlarged front end 444 retains the handle against the base.

FIGS. 32 and 33 are schematic rear cross-sectional views showing valve device 410 in the closed and open positions, respectively. FIG. 32 is a view generally along the line 32-32 in FIG. 31, and FIG. 33 is the same view but after the handle has been twisted about 80 degrees to open the manual valve. One may note, in FIG. 32, that the tab 472 is at one end of the channel 422, the handle bore 424 is about 80 degrees away from the base bore 474 and its associated o-ring, the air passageway is blocked. In FIG. 32, however, the handle 420 has been twisted until the relative rotation of the handle 420 and the base 470 is stopped by the tab abutting into the opposite end of the channel, in which the position bores 424 and bore 474 with its associated o-ring have moved into alignment to open the air passageway.

FIGS. 34-42 portray an alternative embodiment, valve device 510, with many of the features of valve device 310.

Valve device 510, however, comprises a handle 520 and a base 570 that are both asymmetrical around the central axis of the device (also the "rotational axis"), which extends axially through the aperture of the cover 560. As in device 310, the handle is rotatably received around the valve housing 530, which threadably connects and seals to the base 570, for example, by means of o-ring 580. A filter screen is provided across the opening of the o-ring 580 for preventing fouling of the umbrella valve 536 and the central bore of the valve housing, and at least one filtration/dampening pad 539 is placed in front of the umbrella valve 536. Alternatively, other pad(s) and/or screen(s) may be used, with at least one pad/filter being at each of the front and rear of the umbrella valve.

Figure 40:
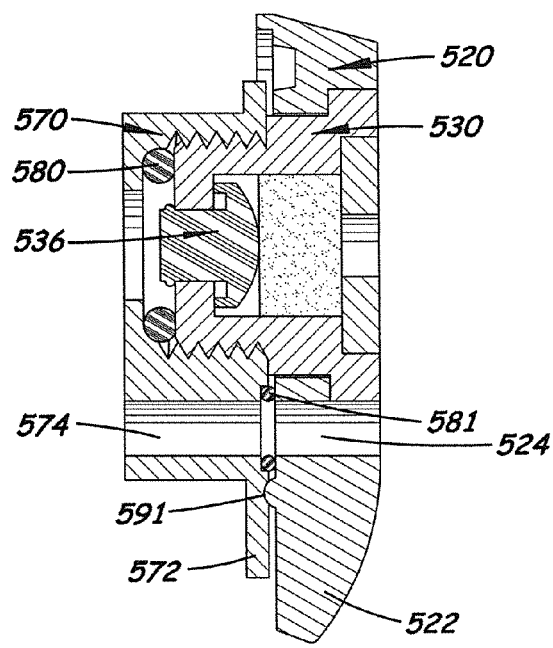
FIG. 40 is a cross-sectional view of the valve device of FIGS. 34-39, shown with the bores in the handle and the base portions aligned so that the manual valve is open. The one-way valve is closed in this figure.

The umbrella valve 536 operates as described above regarding umbrella valve 336 in valve device 310. As discussed earlier, the set-point for automatic expulsion of air around valve 536 may be, for example, in the range of less than or equal to 3 psi differential, and preferably 1-3 psi, or more preferably 1-2 psi, differential (above ambient). The rear end of the stem of umbrella valve 536 is retained in place against forward force by the lip(s) of the stem flaring radially outward to extend along the rear-most surface of the valve housing 530 (FIG. 40). As described above for valve device 310, the lip(s) may alternatively be received in/against a groove or other shelf or radial surface, or less preferably by other means such as adhesive or pin(s) or other fastener(s).

Figures 41, 42:
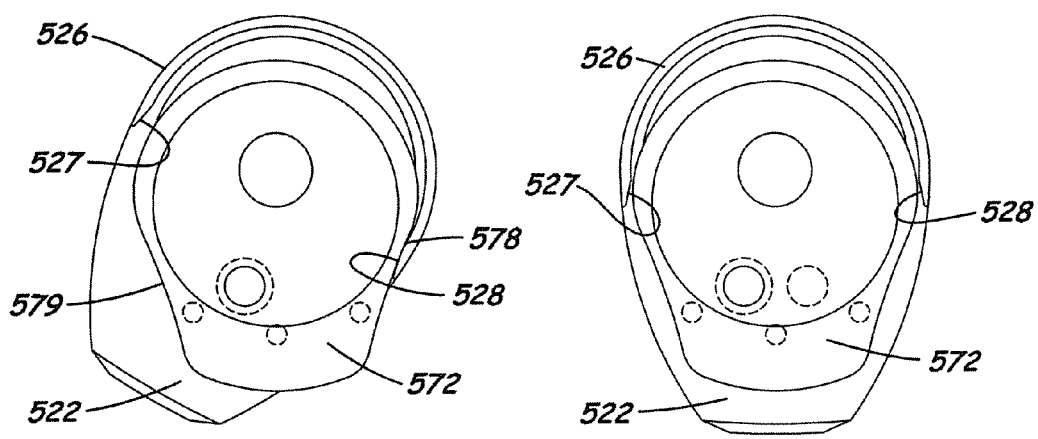
FIG. 41 is a front view of the valve device of FIGS. 34-40, wherein the manual valve is open, that is, the handle has been rotated relative to the base to align the bores for air flow, as in the orientation shown in FIG. 40.
FIG. 42 is a front view of the valve device of FIGS. 34-40, wherein the manual valve is closed, that is, the handle has been rotated to move the bores out of alignment to block air flow (see the separated dashed-line circles).

The base includes an o-ring 581 around the front opening of the base bore 574, which o-ring 581 seals the base bore 574 against the handle rear surface except when the handle is rotated to a full extent to a position wherein the handle bore 524 coaxially aligns with the base bore 574, as shown in FIGS. 40 and 41. Reversing the handle rotation to misalign the bores again closes the manual valve, as shown in FIG. 42.

Therefore, the manual valve operates generally as described above for valve device 310, except that the rotation of the handle is limited by a stop mechanism other than a tab and channel system. The handle is oblong, in other words, elongated in one direction to form a radially-protruding portion 522. The base also is oblong, in other words, elongated in one direction to form a radially-protruding portion 572. The front surface of the base is flat or generally flat, and the rear surface of the handle is flat or generally flat except for a wall 526 and an optional channel 529 of the main body 523 of the handle. The handle and the base front surface may be said to be generally planar, parallel, and coaxial, with rotation of one relative to the other comprising relative rotation in adjacent parallel planes. The rearwardly-extending, circumferential wall 526 extends, for example, in a range of about 200-220 degrees around the outer perimeter of the main body 523. The wall 526 extends axially out along-side a portion of the base, but, since the handle main body 523 has a larger diameter than the base in the region, the wall 526 lies radially outward from the base and does not impede movement of the handle relative to the until the handle is twisted to the limits provided by this stop system. Said limits are when the ends 527, 528 of the wall impact against the outer edge of the protruding region of the base.

The bores are 524, 574 positioned in their respective members so that the valve is closed (the bores are not aligned, or the bores "are angularly distanced") when the protruding region 522 of the handle is aligned over the protruding region 572 of the base, as in FIG. 42. This makes the manual valve easy to close, because the user simply straightens the handle to "point" the same way the base is "pointing"; this position is easy recognize by seeing or feeling the valve device. See FIG. 42. To open the manual valve, the user merely twists the valve until the limit is reached, that is, the handle wall end 528 abuts against the edge/sidewall of the base at location 578. This position coaxially aligns the bores, and may be easily seen or felt to be in the open position because the two protruding regions are offset from each other.

In the embodiment shown in FIGS. 34-42, the handle could also be twisted the opposite direction from that shown FIG. 41, for example, until the wall end 527 abuts against the edge of the base at location 579. This would not align the bores and which would keep the manual valve closed, hence, twisting the handle this direction might be considered unproductive as it doesn't change the status of the manual valve. In certain embodiments, an alternative wall shape or other control may be provided on that side of the valve to prevent or limit the handle from being rotated that "unproductive" direction. One may understand that "mirror image" valves may be made, for example, for placement on a prosthetic on either leg, or, for allowing a user to choose a valve according to his/her preference of opening the valve by twisting the handle toward the front or the rear of his/her body.

Note that optional channel 529 in the rear surface of the handle 520 is for reducing the weight and amount of plastic used in molding of the handle, and not, in this embodiment, for receiving a tab or for being part of rotation-limiting structure. Also, note that protrusions 591 and depressions 592 represent certain embodiments of stabilizing structure, which help maintain the handle in one or the other positions relative to the base (open or closed), thus, preventing the handle from wobbling or moving by accident. The two protrusions 591 "snap" into the center and left depressions 592 (viewed from the rear in FIG. 41), when in the manual-valve-open position. The two protrusions 591 "snap" into the center and right depressions 592 (viewed from the rear in FIG. 42), when in the manual-valve-closed position. It should be noted that other limiting structure and/or other stabilizing structure may be used, but those shown have been found to be effective and economical.

An especially-effective combination of features is found in the embodiment of FIGS. 34-42. Said features comprise the reliable and quick-opening and -sealing systems both for the one-way, expulsion valve, and bore-alignment-based manual valve with an easily-operable handle. Further, the umbrella valve is an especially-preferred and especially-effective one-way valve, wherein the stem snaps through an aperture in a valve housing (that is, the smaller-diameter portion of the central bore) and stretching and/or sliding a very slight amount (for example, in certain embodiments, 0.01-2 mm, 0.05-1 mm, or 0.1-0.5 mm), said slight amount being sufficient for unsealing and releasing of pressure before the umbrella valve resiliently returns to a sealed position. Further, pads and/or screens on each side (front and rear) of the umbrella valve further enhance operation and reliability of the umbrella valve by preventing fouling of the valve. These features are believed to provide quiet, consistent, and effective operation of the twist-open and -close valve device comprising an expulsion valve. Also, the preferred low crack pressure is achievable with the umbrella valve with repeated, consistent operation, and this is important for achieving quiet operation and effective prosthetic suspension without large swings in socket pressure.

Note that various portions of the valve devices may be collectively called "a housing". For example, the base, valve housing with cover (or axle member in embodiments wherein no one-way valve components are provided), and the handle may collectively be called the housing. A portion of the housing, therefore, may be attached to a socket wall, a portion of the housing may be used as a handle to open and close a manual valve, and a portion of the housing may be used to capture/retain the handle in rotatable cooperation with the base and/or to house one-way valve components.

Certain embodiments may therefore be described as a pressure-control system for a prosthetic hard socket, the pressure-control system comprising: a prosthetic socket comprising a wall defining a space for receiving a residual limb, the space comprising a well between the lower end of the limb and the lower end of the socket, wherein a hole extends through said wall in the vicinity of the well; and a valve device comprising: a housing comprising a base at a rear end of the valve device and connected to the socket wall at the hole, and a handle at a front end of the valve device and rotatably connected to the base, wherein each of the base and the handle comprises an axial bore; and wherein the handle is rotatable to an open position wherein the axial bore of the handle is aligned with the axial bore of the base so that the axial bores form an air passageway between the front and rear of the valve device for air-flow from the socket well to the ambient atmosphere outside the socket and air-flow from said ambient atmosphere to the socket well. The handle may be rotatable to a closed position wherein the axial bore of the handle is angularly distanced from the axial bore of the base to block said air passageway. The valve device may comprise an o-ring around the front end of the axial bore of the base, wherein said o-ring seals against a rear surface of the handle when the handle is in the closed position, so that ambient air is prevented from flowing into said axial bore of the base. The handle may be rotatably connected to the base portion by encircling a one-way valve housing portion that is connected to the base portion, and wherein the one-way valve housing portion has a central-bore; and the valve device may further comprise an elastomeric valve member having a rear end retained in the one-way valve housing portion and a flap end that moves between a sealed position against a sealing-surface of the one-way housing position and an unsealed position moved generally forward away from the said sealing-surface. One or more pads may be provided in front of the elastomeric valve member, for example. One or more screens may be behind the elastomeric valve member, for example. The valve device may be described as having a longitudinal axis running between the front end and the rear end, and the base and the handle may be oblong, for example, each comprising a radially-protrusion portion that makes the base and the handle each asymmetrical around the valve device axis. Handle rotation may be in the range of 30-90 degrees between the open position and the closed position. The elastomeric valve member is preferably elastically-biased to the sealed position. The elastomeric valve member may stretch, for example, lengthening, to an unsealed position when pressure in the well builds to a set-point above ambient atmospheric pressure. Also, or instead, the elastomeric valve member flap end may flex forward to the unsealed position when pressure in the well builds to a set-point above ambient atmospheric pressure. Whether the elastomeric valve member stretches and/or flexes to unseat/unseal will depend on the materials and the shape, thickness and overall design of the valve member as will be understood by those of skill in such elastomeric valves, such as polymeric valves including umbrella valves. The set-point may be determined, for example, by selection of the elastomeric valve and is preferably in the range of 1-3 psi differential between pressure in the well and ambient atmospheric pressure. The valve device may comprise a handle-movement limit/stop system, for example, a perimeter wall around a portion of the handle extending axially along-side a portion of the base, wherein an end of the wall abuts into the base to stop rotation of the handle relative to the base when the bores of the handle and base are aligned. To help with ease of use and to help prevent the handle from being opened during normal use of the prosthesis, the radially-protruding portion of the handle and of the base may be adapted to point the same direction when the handle is in the closed position. The radially-protruding portion of the handle may be angularly distanced from the radially-protruding portion of the base when the handle is in the open position. Preferably, the valve device does not comprise a spring.

Certain embodiments may be described as a pressure-control valve device for a prosthetic hard socket, the valve device including a manual two-way valve system comprising: a housing comprising a base for attachment to a prosthetic hard socket, and a handle movably connected to the base, wherein each of the base and the handle comprises an air-flow bore; and wherein the handle is movable to an open position wherein the air-flow bore of the handle is in fluid communication with the air-flow bore of the base so that air flows all the way through the valve device between a front end and a rear end of the valve device. For example, the handle may be generally coaxial with the base and rotate relative to the base on a longitudinal axis of the valve device to said open position. In other words, the handle may be movable in various ways, including but not necessarily limited to rotation relative to the base. In embodiments comprising handle rotation, the handle may rotate relative to the base on said longitudinal axis to move to a closed position wherein the air-flow bore of the handle is not in fluid communication with the air-flow bore of the base so that air does not flow between the front end and the rear end of the valve device. An air-seal is preferably provided around a front end of the air-flow bore of the base, the air-seal sealing against the handle when the handle is moved to the closed position, so that ambient air does not enter the air-flow bore of the base from the front of the base. An automatic one-way expulsion valve member may be provided in addition to the manual valve, to allow the valve device to serve multiple purposes to optimize pressure control inside the socket well. The one-way expulsion valve may be installed in the housing to automatically open when air pressure at a rear end of the expulsion valve member reaches a certain differential pressure above pressure at a front end of the expulsion valve, whereby air flows through the valve device when the manual two-way valve system is closed. Typically, the rear end and front end of the expulsion valve member will be in fluid communication with the rear and the front of the entire valve device, respectively, to provide a second way (in addition to the manual valve) for air flow out of the socket well, with the one-way system typically being for quiet and repeated air expulsion during walking and running. The preferred elastomeric valve member is an umbrella valve.

Although this invention has been described above with reference to particular means, materials and embodiments, it is to be understood that the invention is not limited to these disclosed particulars, but extends instead to all equivalents within the broad scope of the following claims.

The invention claimed is:

1. A pressure-control system for a prosthetic hard socket, the pressure-control system comprising:
    a prosthetic socket comprising a wall defining a space for receiving a residual limb, the space comprising a well between the lower end of the limb and the lower end of the socket, wherein a hole extends through said wall in the vicinity of the well; and
    a valve device comprising:
    a housing comprising a base at a rear end of the valve device and connected to the socket wall at the hole, and a handle at a front end of the valve device and rotatably connected to the base, wherein each of the base and the handle comprises an axial bore; and
    wherein the handle is rotatable to an open position wherein the axial bore of the handle is aligned with the axial bore of the base so that the axial bores form an air passageway between the front and rear of the valve device for air-flow from the socket well to the ambient atmosphere outside the socket and air-flow from said ambient atmosphere to the socket well;
    wherein the handle is rotatable to said open position on a longitudinal axis, both the axial bore of the handle and the axial bore of the base are radially offset from said longitudinal axis, and the handle is rotatable relative to said base on said longitudinal axis to a closed position wherein the axial bore of the handle is angularly distanced from the axial bore of the base to block said air passageway.

2. A pressure control system as in claim 1, wherein the valve device comprises an o-ring around the front end of the axial bore of the base, wherein said o-ring seals against a rear surface of the handle when the handle is in the closed position, so that ambient air is prevented from flowing into said axial bore of the base.

3. A pressure-control system as in claim 1, wherein said handle rotates in the range of 30-90 degrees between the open position and the closed position.

4. A pressure-control system as in claim 3, wherein the valve device comprises a perimeter wall around a portion of the handle extending axially along-side a portion of the base, wherein an end of the wall abuts into the base to stop rotation of the handle relative to the base when the bores of the handle and base are aligned.

5. A pressure-control system as in claim 3, wherein the base and the handle each comprises a radially-protruding portion, and the radially-protruding portions of the handle and of the base point in the same direction when the handle is in the closed position.

6. A pressure-control system as in claim 5, wherein the radially-protruding portion of the handle is angularly distanced from the radially-protruding portion of the base when the handle is in the open position.

7. A pressure-control system for a prosthetic hard socket, the pressure-control system comprising:
    a prosthetic socket comprising a wall defining a space for receiving a residual limb, the space comprising a well between the lower end of the limb and the lower end of the socket, wherein a hole extends through said wall in the vicinity of the well; and
    a valve device comprising:
    a housing comprising a base at a rear end of the valve device and connected to the socket wall at the hole, and a handle at a front end of the valve device and rotatably connected to the base, wherein each of the base and the handle comprises an axial bore; and
    wherein the handle is rotatable to an open position wherein the axial bore of the handle is aligned with the axial bore of the base so that the axial bores form an air passageway between the front and rear of the valve device for air-flow from the socket well to the ambient atmosphere outside the socket and air-flow from said ambient atmosphere to the socket well; wherein:
        the handle is rotatably connected to the base portion by encircling a one-way valve housing portion that is connected to the base portion, and wherein the one-way valve housing portion has a central-bore; and
        the valve device further comprises an elastomeric valve member having a rear end retained in the one-way valve housing portion and a flap end that moves between a sealed position against a sealing-surface of the one-way housing position and an unsealed position moved generally forward away from the said sealing-surface.

8. A pressure control system as in claim 7, further comprising at least one pad in front of the elastomeric valve member.

9. A pressure control system as in claim 8, further comprising at least one screen behind the elastomeric valve member.

10. A pressure-control system as in claim 7, wherein the elastomeric valve member is elastically-biased to the sealed position.

11. A pressure-control system as in claim 10, wherein the elastomeric valve member stretches to an unsealed position when pressure in the well builds to a set-point above ambient atmospheric pressure.

12. A pressure-control system as in claim 11, wherein the set-point is in the range of 1-3 psi differential between pressure in the well and ambient atmospheric pressure.

13. A pressure-control system as in claim 10, wherein the elastomeric valve member flap end flexes forward to the unsealed position when pressure in the well builds to a set-point above ambient atmospheric pressure.

14. A pressure-control system as in claim 13, wherein the set-point is in the range of 1-3 psi differential between pressure in the well and ambient atmospheric pressure.

15. A pressure-control system as in claim 10, comprising no spring.

16. A pressure-control system as in claim 7, comprising no spring.

17. A pressure control system for a prosthetic hard socket, the pressure-control system comprising:
 a prosthetic socket comprising a wall defining a space for receiving a residual limb, the space comprising a well between the lower end of the limb and the lower end of the socket, wherein a hole extends through said wall in the vicinity of the well; and
 a valve device comprising:
  a housing comprising a base at a rear end of the valve device and connected to the socket wall at the hole, and a handle at a front end of the valve device and rotatably connected to the base, wherein each of the base and the handle comprises an axial bore; and
  wherein the handle is rotatable to an open position wherein the axial bore of the handle is aligned with the axial bore of the base so that the axial bores form an air passageway between the front and rear of the valve device for air-flow from the socket well to the ambient atmosphere outside the socket and air-flow from said ambient atmosphere to the socket well;
 wherein the valve device has a longitudinal axis from the front end to the rear end, and the base and the handle each comprises a radially-protruding portion that makes the base and the handle each asymmetric around the valve device longitudinal axis.

18. A pressure-control system as in claim 17, wherein said handle rotates in the range of 30-90 degrees between the open position and a closed position.

19. A pressure-control system as in claim 18, wherein the valve device comprises a perimeter wall around a portion of the handle extending axially along-side a portion of the base, wherein an end of the wall abuts into the base to stop rotation of the handle relative to the base when the bores of the handle and base are aligned.

20. A pressure-control system as in claim 18, wherein the radially-protruding portions of the handle and of the base point in the same direction when the handle is in the closed position.

21. A pressure-control system as in claim 20, wherein the radially-protruding portion of the handle is angularly distanced from the radially-protruding portion of the base when the handle is in the open position.

22. A pressure-control valve device for a prosthetic hard socket, the valve device including a manual two-way valve system comprising:
 a housing comprising a base for attachment to a prosthetic hard socket, and a handle movably connected to the base, wherein each of the base and the handle comprises an axial air-flow bore; and
 wherein the handle is moveable relative to the base to an open position wherein the axial air-flow bore of the handle is in fluid communication with the axial air-flow bore of the base so that air flows all the way through the valve device between a front end and a rear end of the valve device; and
 wherein the handle is moveable relative to said base to a closed position wherein the axial air-flow bore of the handle is distanced from the axial air-flow bore of the base to block said air passageway;
 wherein the handle is generally coaxial with the base and moves by rotating relative to the base on a longitudinal axis between the front end and the rear end of the valve device to said open position;
 wherein the handle rotates relative to the base on said longitudinal axis to move to the closed position wherein the air-flow bore of the handle is not in fluid communication with the air-flow bore of the base so that air does not flow between the front end and the rear end of the valve device;
 further comprising an automatic one-way expulsion valve member in the housing that automatically opens when air pressure at a rear end of the expulsion valve member reaches a certain differential pressure above pressure at a front end of the expulsion valve, whereby air flows through the valve device when the manual two-way valve system is closed;
 wherein the elastomeric valve member is an umbrella valve.

23. A valve device as in claim 22, comprising no spring.

* * * * *